(12) United States Patent
Honour et al.

(10) Patent No.: US 8,147,486 B2
(45) Date of Patent: Apr. 3, 2012

(54) MEDICAL DEVICE WITH FLEXIBLE PRINTED CIRCUIT

(75) Inventors: Kirk S. Honour, Minnetonka, MN (US); Michael J. Johnson, Minneapolis, MN (US); Gabriel A. Mouchawar, Valencia, CA (US); Jeremy D. Dando, Plymouth, MN (US); Christine M. Byam, Plymouth, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1350 days.

(21) Appl. No.: 11/752,755

(22) Filed: May 23, 2007

(65) Prior Publication Data
US 2007/0219551 A1      Sep. 20, 2007

Related U.S. Application Data

(63) Continuation-in-part of application No. 10/668,843, filed on Sep. 22, 2003, now Pat. No. 7,229,437.

(51) Int. Cl.
*A61B 18/14* (2006.01)
*A61B 18/18* (2006.01)

(52) U.S. Cl. ............................... 606/41; 607/96; 607/101

(58) Field of Classification Search ............... 606/41–50; 607/96–107
See application file for complete search history.

(56) References Cited

U.S. PATENT DOCUMENTS

| | | |
|---|---|---|
| 3,867,945 A | 2/1975 | Long |
| 4,033,331 A | 7/1977 | Guss et al. |
| 4,117,836 A | 10/1978 | Erickson |
| 4,244,362 A | 1/1981 | Anderson |
| 4,445,892 A | 5/1984 | Hussein et al. |
| 4,500,529 A | 2/1985 | Shanklin, Jr. et al. |
| 4,558,155 A | 12/1985 | Shanklin, Jr. et al. |
| 4,569,347 A | 2/1986 | Frisbie |
| 4,581,017 A | 4/1986 | Sahota |
| 4,641,649 A | 2/1987 | Walinsky et al. |
| 4,705,517 A | 11/1987 | DiPisa, Jr. |
| 4,721,117 A | 1/1988 | Mar et al. |
| 4,729,384 A | 3/1988 | Bazenet |
| 4,790,331 A | 12/1988 | Okada et al. |
| 4,810,244 A | 3/1989 | Allen |

(Continued)

FOREIGN PATENT DOCUMENTS
DE      4001086      7/1991
(Continued)

OTHER PUBLICATIONS

Cox, James L. et al., "Electrophysiology, Pacing, and Arrhythmia, "Operations for Atrial Fibrillation"", *Clin. Cardiol.* vol. 14, Oct. 1991, 827-834.

(Continued)

*Primary Examiner* — Roy Gibson
(74) *Attorney, Agent, or Firm* — Wiley Rein LLP

(57) ABSTRACT

A catheter or lead having a flexible printed circuit for conveying signals and/or energy. Each trace may be in electrical connection with one or more external electrical contacts. More specifically, each trace is typically electrically connected to a single contact. The traces and contacts may assist in diagnosis and/or detection of bio-electrical signals emitted by organs, and may transmit such signals to a connector or diagnostic device affixed to the catheter. The external electrical contacts may detect bioelectric energy or may deliver electrical or thermal energy to a target site.

29 Claims, 15 Drawing Sheets

U.S. PATENT DOCUMENTS

| | | | |
|---|---|---|---|
| 4,838,879 | A | 6/1989 | Tanabe et al. |
| 4,867,174 | A | 9/1989 | Skribiski |
| 4,882,777 | A | 11/1989 | Narula |
| 4,883,058 | A | 11/1989 | Ruiz |
| 4,890,623 | A * | 1/1990 | Cook et al. .................. 600/374 |
| 4,898,591 | A | 2/1990 | Jang et al. |
| 4,911,163 | A | 3/1990 | Fina |
| 4,917,102 | A | 4/1990 | Miller et al. |
| 4,935,017 | A | 6/1990 | Sylvanowicz |
| 4,945,912 | A | 8/1990 | Langberg |
| 4,955,377 | A | 9/1990 | Lennox et al. |
| 4,969,875 | A | 11/1990 | Ichikawa |
| 4,988,698 | A | 1/1991 | Kato et al. |
| 5,002,532 | A | 3/1991 | Gaiser et al. |
| 5,016,640 | A | 5/1991 | Ruiz |
| 5,052,407 | A | 10/1991 | Hauser et al. |
| 5,100,388 | A | 3/1992 | Behl et al. |
| 5,103,804 | A | 4/1992 | Abele |
| 5,106,360 | A | 4/1992 | Ishiwara et al. |
| 5,109,851 | A * | 5/1992 | Jadvar et al. .................. 600/439 |
| 5,120,323 | A | 6/1992 | Shockey et al. |
| 5,147,315 | A | 9/1992 | Weber |
| 5,162,911 | A | 11/1992 | Burrage |
| 5,171,232 | A | 12/1992 | Castillo et al. |
| 5,172,699 | A | 12/1992 | Svenson et al. |
| 5,209,229 | A | 5/1993 | Gilli |
| 5,215,540 | A | 6/1993 | Anderhub |
| 5,215,989 | A | 6/1993 | Baldwin et al. |
| 5,222,501 | A | 6/1993 | Ideker et al. |
| 5,228,442 | A | 7/1993 | Imran |
| 5,231,994 | A | 8/1993 | Harmjanz |
| 5,231,995 | A | 8/1993 | Desai |
| 5,242,441 | A | 9/1993 | Avitall |
| 5,246,007 | A | 9/1993 | Frisbie et al. |
| 5,246,438 | A | 9/1993 | Langberg |
| 5,256,141 | A | 10/1993 | Gencheff et al. |
| 5,263,493 | A | 11/1993 | Avitall |
| 5,267,982 | A | 12/1993 | Sylvanowicz et al. |
| 5,271,392 | A | 12/1993 | Ferek-Petric |
| 5,279,546 | A | 1/1994 | Mische et al. |
| 5,281,213 | A | 1/1994 | Milder et al. |
| 5,281,217 | A | 1/1994 | Edwards et al. |
| 5,281,218 | A | 1/1994 | Imran |
| 5,282,836 | A | 2/1994 | Kreyenhagen et al. |
| 5,286,866 | A | 2/1994 | Carr et al. |
| 5,287,858 | A | 2/1994 | Hammerslag et al. |
| 5,290,229 | A | 3/1994 | Paskar |
| 5,293,868 | A | 3/1994 | Nardella |
| 5,295,493 | A | 3/1994 | Radisch |
| 5,299,574 | A | 4/1994 | Bower |
| 5,304,131 | A | 4/1994 | Paskar |
| 5,304,214 | A | 4/1994 | DeFord et al. |
| 5,312,355 | A | 5/1994 | Lee |
| 5,322,509 | A | 6/1994 | Rickerd |
| 5,359,760 | A | 11/1994 | Busse et al. |
| 5,366,443 | A | 11/1994 | Eggers et al. |
| 5,366,490 | A | 11/1994 | Edwards et al. |
| 5,417,208 | A | 5/1995 | Winkler |
| 5,427,119 | A | 6/1995 | Swartz et al. |
| 5,433,729 | A | 7/1995 | Adams et al. |
| 5,450,846 | A | 9/1995 | Goldreyer |
| 5,462,529 | A | 10/1995 | Simpson et al. |
| 5,468,239 | A | 11/1995 | Tanner et al. |
| 5,472,441 | A | 12/1995 | Edwards et al. |
| 5,476,495 | A | 12/1995 | Kordis et al. |
| 5,484,412 | A | 1/1996 | Pierpont et al. |
| 5,497,774 | A | 3/1996 | Swartz et al. |
| 5,536,247 | A | 7/1996 | Thornton |
| 5,540,679 | A | 7/1996 | Fram et al. |
| 5,564,440 | A | 10/1996 | Swartz et al. |
| 5,575,766 | A | 11/1996 | Swartz et al. |
| 5,584,872 | A | 12/1996 | LaFontaine et al. |
| 5,588,961 | A | 12/1996 | Leone et al. |
| 5,599,307 | A | 2/1997 | Bacher et al. |
| 5,624,439 | A | 4/1997 | Edwards et al. |
| 5,628,316 | A | 5/1997 | Swartz et al. |
| 5,640,955 | A | 6/1997 | Ockuly et al. |
| 5,676,693 | A | 10/1997 | LaFontaine |
| 5,681,308 | A | 10/1997 | Edwards et al. |
| 5,722,400 | A | 3/1998 | Ockuly et al. |
| 5,746,495 | A | 5/1998 | Klamm |
| 5,779,644 | A | 7/1998 | Eberle et al. |
| 5,785,706 | A | 7/1998 | Bednarek |
| 5,792,105 | A | 8/1998 | Lin et al. |
| 5,797,905 | A | 8/1998 | Fleischman et al. |
| 5,800,482 | A | 9/1998 | Pomeranz et al. |
| 5,803,083 | A | 9/1998 | Buck et al. |
| 5,807,306 | A | 9/1998 | Shapland et al. |
| 5,814,029 | A | 9/1998 | Hassett |
| 5,824,026 | A | 10/1998 | Diaz |
| 5,938,660 | A | 8/1999 | Swartz et al. |
| 5,971,983 | A | 10/1999 | Lesh |
| 6,068,629 | A | 5/2000 | Haissaguerre et al. |
| 6,097,976 | A | 8/2000 | Yang et al. |
| 6,120,500 | A | 9/2000 | Bednarek et al. |
| 6,156,018 | A | 12/2000 | Hassett |
| 6,185,449 | B1 | 2/2001 | Berg et al. |
| 6,213,995 | B1 | 4/2001 | Steen et al. |
| 6,235,025 | B1 | 5/2001 | Swartz et al. |
| 6,251,109 | B1 | 6/2001 | Hassett et al. |
| 6,357,447 | B1 * | 3/2002 | Swanson et al. ............... 128/898 |
| 6,360,128 | B2 | 3/2002 | Kordis et al. |
| 6,503,247 | B2 | 1/2003 | Swartz et al. |
| 6,526,302 | B2 | 2/2003 | Hassett |
| 6,540,744 | B2 | 4/2003 | Hassett et al. |
| 6,976,986 | B2 | 12/2005 | Berube |
| 2003/0176905 | A1 * | 9/2003 | Nicolelis et al. ............... 607/116 |
| 2004/0024397 | A1 | 2/2004 | Griffin et al. |
| 2005/0060885 | A1 | 3/2005 | Johnson et al. |
| 2005/0065505 | A1 | 3/2005 | Ryan |

FOREIGN PATENT DOCUMENTS

| | | |
|---|---|---|
| EP | 656217 | 11/1997 |
| EP | 670168 | 12/1998 |
| WO | WO92-12754 | 8/1992 |
| WO | 9219307 | 11/1992 |
| WO | WO96-00042 | 1/1996 |
| WO | WO97-16127 | 5/1997 |

OTHER PUBLICATIONS

Cox, James L. et al., "The surgical treatment of atrial fibrillation", *J Thorac Cardiovasc Surgery*, vol. 101 1991, 406-426.

Cox, James L. et al., "The surgical treatment of atrial fibrillation", *The Journal of Thoracic and Cardiovascular Surgery*, vol. 101 Apr. 1991, 569-583.

Cox, James L., "The surgical treatment of atrial fibrillation", *J Thorac Cardiovasc Surgery*, vol. 101 1991, 584-592.

Gallagher, John J. et al., "Catheter Technique for Closed-Chest Ablation of the Atrioventricular Conduction System", *The New England Journal of Medicine*, vol. 305 Jan. 28, 1982, 194-200.

Haissaguerre, Michel et al., "Right and Left Atrial Radiofrequency Catheter Therapy of Paroxysmal Atrial Fibrillation", *Journal of Cardiovascular Elecrtrophysiology*, vol. 7, No. 12 Dec. 1996, 1132-1144.

Heinz, Gottfried et al., "Improvement in Left Ventricular Systolic Function After Successful Radiofrequency His Bundle Ablation for Drug Refractory, Chronic Atrial Fibrillation and Recurrent Atrial Flutter", *Journal of Cardiology*, vol. 69 Feb. 15, 1992, 489-492.

Horowitz, Leonard N. et al., "Current Management of Arrhythmias—Catheter Ablation", 1991, 373-378.

Huang, Shoei K. et al., "Closed Chest Catheter Desiccation of the Atrioventricular Junction Using Radiofrequency Energy—A New Method of Catheter Ablation", *Journal of the American College of Cardiology*, vol. 9, No. 2 1987, 349-358.

Martin, David et al., "Atrial Fibrillation", 1994, 35-59.

Saul, Philip J. et al., "Catheter Ablation of Accessory Atrioventricular Pathways in Young Patients: Use of Long Vascular Sheaths, the Transseptal Approach and a Retrograde Left Posterior Parallel Approach", *Journal of the Americal College of Cardiology*, vol. 21, No. 3 Mar. 1, 1993, 571-583.

Scheinman, Melvin M. et al., "Catheter-Induced Ablation of the Atrioventricular Junction to Control Refractory Supraventricular Arrhythmias", *The Journal of the American Medical Association*, vol. 248, No. 7 Aug. 20, 1082, 851-855.

Singer, Igor et al., "Catheter Ablation for Arrhythmias", *Clinical Manual of Electrophysiology* 1993, 421-431.

Swartz, John F. et al., "Radiofrequency Endocardial Catheter Ablation of Accessory Atrioventricular Pathway Atrial Insertion Sites", *American Heart Association, Circulation*, vol. 87, No. 2 Feb. 1993, 487-499.

Tracy, Cynthia M. et al., "Radiofrequency Catheter Ablation of Ectopic Atrial Tachycardia Using Paced Activation Sequence Mapping", *Journal of the American College of Cardiology*, vol. 21, No. 4 Mar. 15, 1993, 910-917.

\* cited by examiner

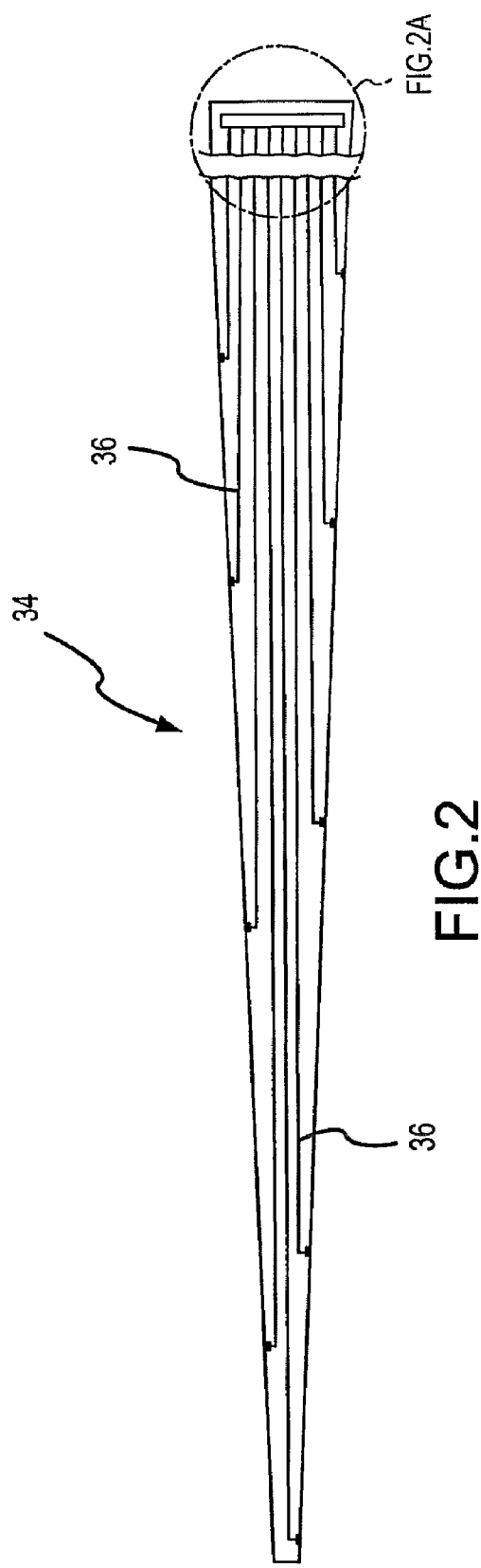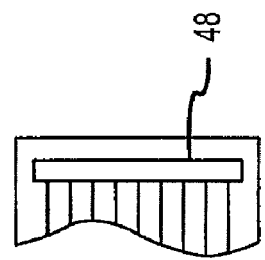
FIG.2
FIG.2A

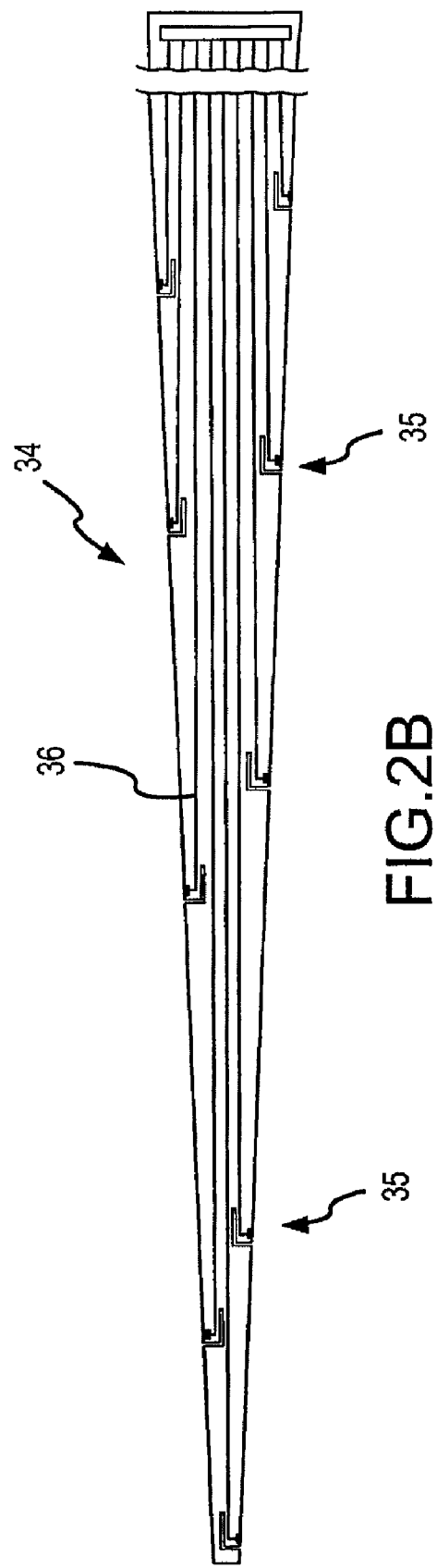

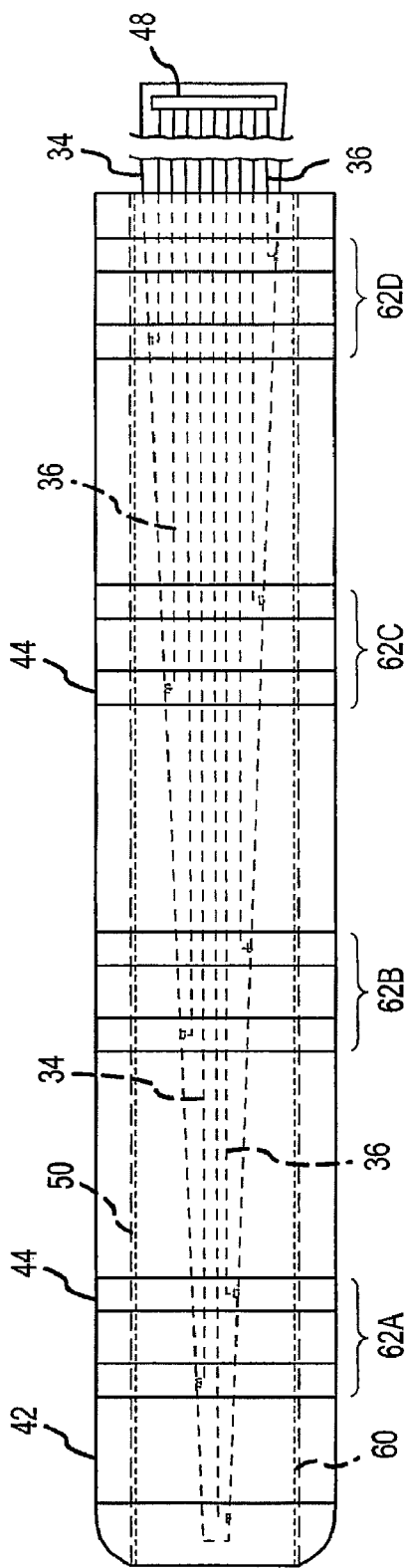
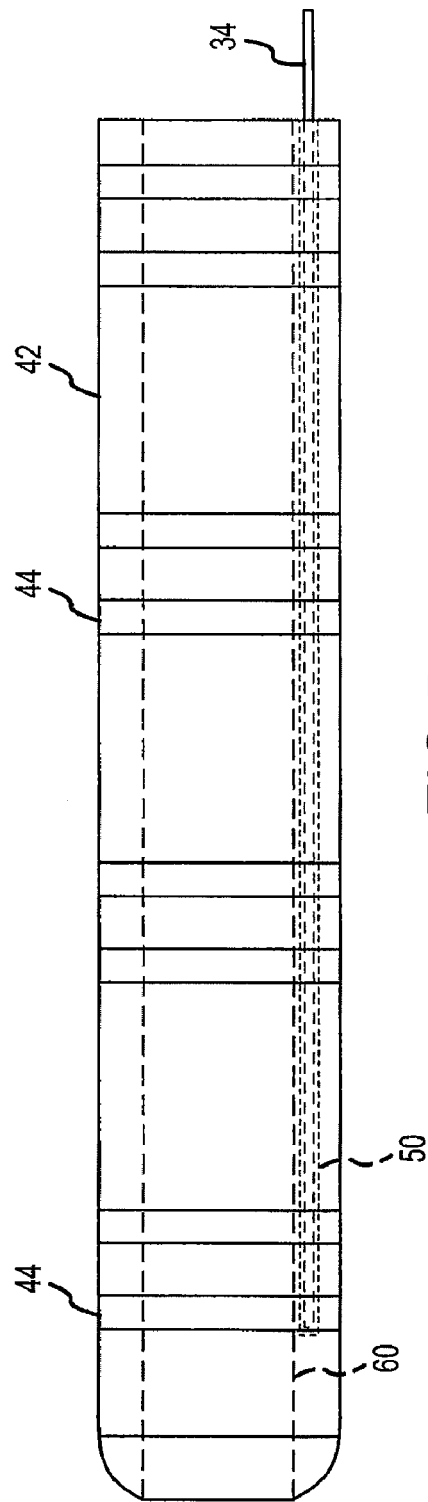
FIG.4
FIG.5

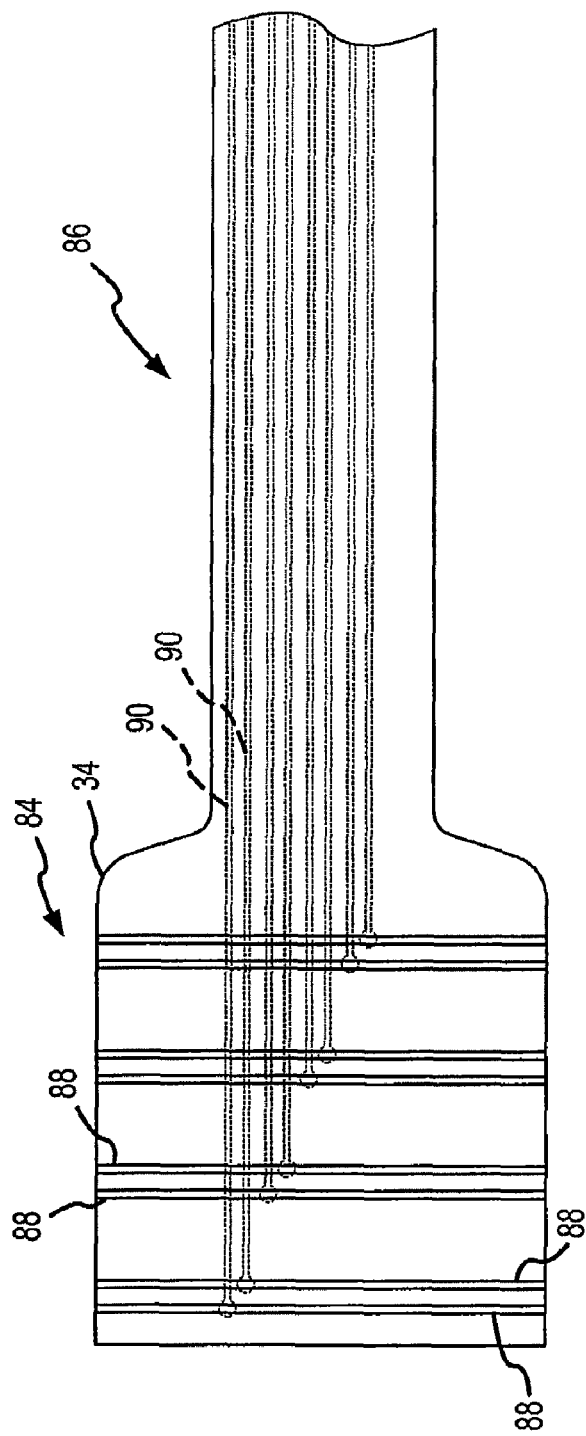
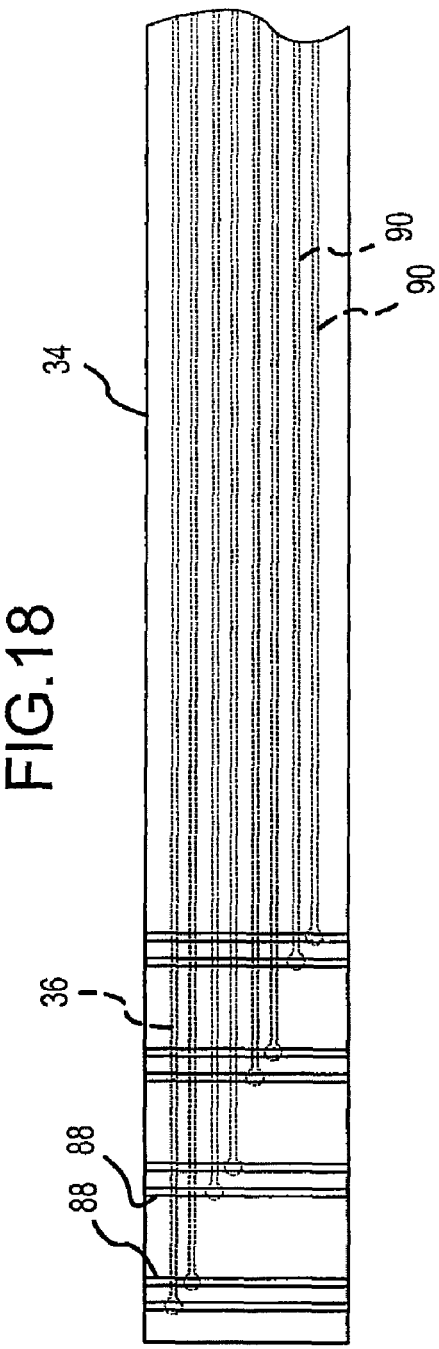
FIG.18
FIG.19

MEDICAL DEVICE WITH FLEXIBLE PRINTED CIRCUIT

CROSS-REFERENCE TO RELATED APPLICATIONS

This application is a continuation-in-part of U.S. application Ser. No. 10/668,843, filed 22 Sep. 2003 now U.S. Pat. No. 7,229,437 (the '843 application). The '843 application is hereby incorporated by reference in its entirety as though fully set forth herein.

BACKGROUND OF THE INVENTION a. Field of the Invention

The invention relates generally to the field of medical instruments, and more particularly to a medical instrument for introduction into a body, such as a catheter, diagnostic catheter, ablation catheter, pacemaker, and internal cardiac defibrillator, that employs a flexible printed circuit to convey signals or energy along the medical device. The invention also relates to manufacturing methods for producing such medical instruments.

b. Background Art

Catheters have been used for medical procedures for many years. Among other uses, physicians use catheters to examine, diagnose, and/or treat tissue while positioned at a specific location within the body otherwise inaccessible without more invasive procedures. Increasingly, catheters are used for medical procedures involving the human heart.

As illustrated in FIG. 1, a typical human heart 10 includes a right ventricle 12, a right atrium 14, a left ventricle 16 and a left atrium 18. The right atrium is in fluid communication with the superior vena cava 20 and the inferior vena cava 22. The interatrial septum 24 separates the right atrium from the left atrium. The tricuspid valve 26 provides a fluid flow path between the right atrium and the right ventricle. On the inner wall of the right atrium where it is connected with the left atrium is a thin walled, recessed area, referred to as the fossa ovalis 28. Between the fossa ovalis and the tricuspid valve is the opening or ostium for the coronary sinus 30. The coronary sinus is the large epicardial vein which accommodates most of the venous blood which drains from the myocardium into the right atrium.

In a normal heart, contraction and relaxation of the heart muscle (myocardium), i.e., the "heart beats," takes place in an organized fashion as electrochemical signals pass sequentially through the myocardium from the sinoatrial (SA) node (not shown) located in the right atrium 14 to the atrialventricular (AV) node (not shown) and then along a well defined route, which includes the His-Purkinje system, into the left 16 and right 12 ventricles. Normally, initial electric impulses are generated at the SA node and conducted to the AV node. The AV node lies near the ostium of the coronary sinus 30. The His-Purkinje system begins at the AV node and penetrates the membranous interatrial septum 24 into the membranous interventricular septum 32. At the basilar aspect (or upper aspect/superior aspect) of the interventricular septum, the His-Purkinje system splits into right and left branches which straddle the summit of the muscular part of the interventricular septum.

Sometimes abnormal rhythms occur in one or both atria which are referred to as atrial arrhythmia. Three of the most common arrhythmia are ectopic atrial tachycardia, atrial fibrillation and atrial flutter. Atrial arrhythmia can have various impacts on a patient. For example, atrial fibrillation can result in significant patient discomfort and even death because of a number of associated problems, including the following: (1) an irregular heart rate, which causes a patient discomfort and anxiety, (2) loss of synchronous atrioventricular contractions which compromises cardiac hemodynamics resulting in varying levels of congestive heart failure, and (3) stasis of blood flow, which increases the vulnerability to thromboembolism and the associated risk of stroke.

It is sometimes difficult to isolate a specific pathological cause for the atrial fibrillation although it is believed that the principal mechanism is one or a multitude of extra circuits within the left and/or right atrium. These extra circuits, which are also sometimes referred to as extra electrical pathways, may interfere with the normal electrochemical signals passing from the SA node to the AV node and into the ventricles. Efforts to alleviate these problems in the past have included significant usage of various drugs. In some circumstances drug therapy is ineffective and frequently is plagued with side effects such as dizziness, nausea, vision problems, and other difficulties.

A procedure, oftentimes referred to as "mapping," utilizes a catheter with sensing electrodes to monitor various forms of electrical activity in the human body. Various organs, including the heart and brain, may be mapped by a catheter having appropriate diagnostic functions. Through mapping, a physician can, in some instances, detect the extra electrical pathways believed to cause the abnormal rhythms. Moreover, the physician can determine the presence or general location of the pathways.

Upon detection of extra pathways causing an irregular heartbeat, an increasingly common medical procedure for the treatment of certain types of cardiac arrhythmia and atrial arrhythmia uses a catheter to convey energy to a selected location within the heart to cauterize or necrotize cardiac tissue and thereby cut off the path for extra or improper electrical signals. This procedure is often referred to as an "ablation" of cardiac tissue. Typically, the ablation catheter is inserted in an artery or vein in the leg, neck, or arm of the patient and threaded, through an introducer, through the vessels until the ablation catheter reaches the desired location for the ablation procedure in the heart. One type of ablation catheter commonly used to perform ablation produces lesions or small burns that electrically isolate or render the tissue non-conductive at particular points in the cardiac tissue by physical contact of the cardiac tissue with an electrode of the ablation catheter and application of energy, such as radio frequency energy. The lesion partially or completely blocks the extra electrical pathways to lessen or eliminate arrhythmias.

In some respects, mapping may be thought of as the opposite of ablation. Specifically, a mapping catheter detects bioelectric impulses generated by the tissue in question and relays these bioelectric impulses to a diagnostic machine operably attached to the catheter. Accordingly, instead of transmitting energy to tissue, the mapping catheter transmits signals from the tissue and can be read in the form of voltages.

Regardless of the direction of energy transmission, present catheters generally mechanically mount the bioelectric receivers and energy delivery media, such as electrodes, to the catheter surface. Further, the transmission media, typically one or more wires, is generally strung through an opening in the center of the catheter, and is not attached to the catheter save at the connection point with the electrodes. Accordingly, as the catheter is steered, bent, and moved during a procedure, stress may be applied to the internal wires.

In some instances, a catheter may also provide a conduit by which other catheter or medical devices are inserted into a patient. When medical instruments are inserted into the catheter interior, the surgeon must exercise some degree of care to ensure the instruments do not interfere with the diagnostic functions of the catheter or, possibly, damage the wires.

Catheters used in mapping and ablation can be very small in diameter. For example, some catheters are as small as 2 to 6 French (1 French=0.3 mm), and can be smaller. As such, assembly of a catheter, such as connecting wires to the electrode and stringing those wires through the catheter can be difficult. In some instances, due to the difficulty in adhering the wires to the electrodes, defective catheters may be produced, resulting in poor signals, waste and lowered manufacturing efficiency.

Oftentimes it is necessary to drill or pierce holes through the catheter in order to connect the wires to electrodes. If not properly sealed, fluid can seep into the holes and cause distortion of the signals, cause shorting, and cause other problems.

Further, many diagnostic and energy delivery catheters have multiple wires running to a variety of diagnostic or energy delivery sites. At the catheter's distal end, these wires often simply terminate with little or no identification separating one wire from the next, making attaching a wire to the appropriate connector pin of a medical device difficult. Apparatus leads, such as pacemaker leads, often suffer from similar problems. Leads may be used to deliver energy to tissue, typically in order to regulate tissue contraction through timed pulses of electricity. Such regulation may occur, for example, by a pacemaker or ICD.

Accordingly, there is a need for an improved medical device capable of transmitting electrical energy across its length either to or from a target site.

BRIEF SUMMARY OF THE INVENTION

Aspects of the present invention involve a catheter or other medical device employing a printed circuit, such as a flexible printed circuit board, with conductive traces to convey signals to and from one or more electrodes along the catheter. One aspect of the invention involves a medical device for introduction into a human body comprising a generally tubular body; at least one electrode coupled with the tubular body; and at least one printed circuit comprising at least one conductive trace in communication with the at least one electrode. The at least one printed circuit may comprise at least one flexible printed circuit. The tubular body may comprise at least one lumen housing the printed circuit. Alternatively, the tubular body may define a cylindrical outside surface with the printed circuit coupled with the outside surface.

The electrode may be adapted to receive signals, such as bioelectric impulses, from a target tissue, such as the heart. The electrode may also be adapted to convey energy, such as ablation energy, to a target tissue. In one particular aspect of the invention, the medical device further comprises at least one wire in communication with at least one tip electrode. The tip electrode may be adapted to sense or convey signals.

In another particular aspect of the invention, the medical device comprises a plurality of electrodes in communication, either directly or indirectly, with a plurality of traces. The conductive traces are also in communication, either directly or indirectly, with a connector.

In another particular aspect of the invention, the medical device may employ more that one printed circuit. For example, the medical device may comprise a first printed circuit defining at least one first conductive trace and a second printed circuit defining at least one second conductive trace. In this example, the at least one first conductive trace is in communication with the at least one second conductive trace.

The conductive traces may be deployed as the electrode. The electrode may also be a ring electrode, tip electrode, or any other conventional electrode capable of use in a medical device. For coupling to a ring electrode, the at least one conductive trace may be circumferentially coupled with the tubular body. The electrode ring may then be coupled with the at least one circumferentially arranged conductive trace.

The tubular body of the medical device may define a tip, a shaft, be flexible, include a steering mechanism, define a catheter, define an ablation medical device (e.g., an ablation catheter), define a diagnostic medical device, define an internal cardiac defibrillator lead, and define a pacing lead.

A second aspect of the invention involves a catheter comprising: a generally tubular body; at least one supporting member at least partially within the tubular body, the at least one supporting member defining at least one aperture; and, at least one printed circuit, such as a flexible printed circuit, defining at least one conductive trace, the at least one printed circuit arranged within the at least one aperture of the at least one supporting member. The supporting member may define a ring-shaped member and may comprise an electrode, such as a ring electrode. The electrode is electrically connected with the conductive trace of the printed circuit.

In one particular aspect, the ring-shaped member may define a radially arranged aperture housing a conductor to electrically connect the conductive trace to the electrode. The conductor may be solder, solder paste, a wire or a trace. The ring-shaped member may define an outside circumference wherein the electrode is affixed to at least a portion of the outside circumference. Alternatively, the ring-shaped member may be at least partially formed of a conductive material and integrally define an electrode. The at least one supporting member may be integrally formed in the tubular body.

A third aspect of the present invention involves a method of manufacturing a medical device comprising: arranging a support member in a fixture, the support member defining at least one longitudinally arranged aperture; arranging a printed circuit board in the at least one longitudinally arranged aperture such that one of at least one conductive traces defined on the printed circuit board is aligned with the at least one longitudinally arranged aperture; placing the fixture in an injection mold defining at least a portion of the medical device; and injecting mold material into the mold. The support member may be a ring-shaped support member. Further, the ring-shaped support member may include an electrode with a conductor provided between the electrode and the at least one conductive trace.

In one particular aspect, the manufacturing method may further comprise attaching a ring-shaped electrode to the ring-shaped support member; and, providing a conductor between the ring-shaped electrode and the at least one conductive trace. Further, solder paste may be arranged to form an electrical contact between the ring-shaped electrode and the conductive trace.

In another particular aspect, the ring-shaped support member may define a radially disposed aperture, and the manufacturing method may further comprise arranging solder paste at least partially within the radially disposed aperture such that the solder paste forms an electrical contact between the electrode and the at least one conductive trace.

A fourth aspect of the invention involves a second method of manufacturing a medical device comprising: obtaining a generally tubular body defining an outside surface; obtaining a flexible printed circuit comprising at least one conductive trace; and, bending the flexible printed circuit board around the outside surface of the generally tubular body. The method may further comprise affixing the flexible printed circuit board to the outside surface of the generally tubular body. The flexible printed circuit board may define at least one first conductive trace and at least one second conductive trace generally perpendicularly arranged with respect to the first conductive trace. The method may further comprise bending the flexible printed circuit such that the first conductive trace is arranged generally circumferentially and the second conductive trace is arranged generally longitudinally.

Other aspects of the method may include electrically connecting a ring electrode to the first conductive trace, such as wherein the first conductive trace defines an electrode surface or wherein the second conductive trace is arranged to convey signals to and from the first conductive trace.

A fifth aspect of the invention involves a flexible printed circuit board adapted for use with a medical device comprising: a flexible substrate defining a first section and a second section, the first section being narrower than the second section; the flexible substrate further defining at least one first conductive trace and at least one second conductive trace, the at least one first conductive trace being arranged generally angularly to the at least one second trace; the at least one first conductive trace is arranged along the first section of the flexible substrate; and, the at least one second conductive trace is arranged generally longitudinally along at least a portion of the second section.

The at least one first conductive trace may be arranged generally perpendicular to the at least one second trace. The first conductive trace is electrically connected with the second conductive trace. The first conductive trace may comprise a plurality of conductive traces, and the second conductive trace may comprise a plurality of conductive traces wherein each of the plurality of first conductive traces are only electrically connected with one of the plurality of second conductive traces. The first conductive trace may be at least partially exposed. Finally, the second conductive trace may be electrically isolated within the flexible printed circuit except for the connection to the at least one first conductive trace.

These and other aspects of the invention are described in further detail below and shown in the accompanying drawings.

BRIEF DESCRIPTION OF THE DRAWINGS

FIG. 2 is a top view of one implementation of a flexible printed circuit for use in a catheter, in accordance with the present invention.

FIG. 2A is a top close up view of a connector of the flexible printed circuit of FIG. 2, in accordance with the present invention.

FIG. 2B is top view of an alternative implementation of a flexible printed circuit for use in a catheter, in accordance with the present invention.

FIG. 4 is a partial top view of a distal tip region of one implementation of a catheter showing a flexible printed circuit in hidden line.

FIG. 5 is a partial side view of catheter of FIG. 4.

FIG. 18 is a top view of one implementation of a flexible printed circuit for use in a catheter, in accordance with the present invention.

FIG. 19 is a top view of an alternative implementation of a flexible printed circuit for use in a catheter, in accordance with the present invention.

DETAILED DESCRIPTION OF THE INVENTION

Figure 1:
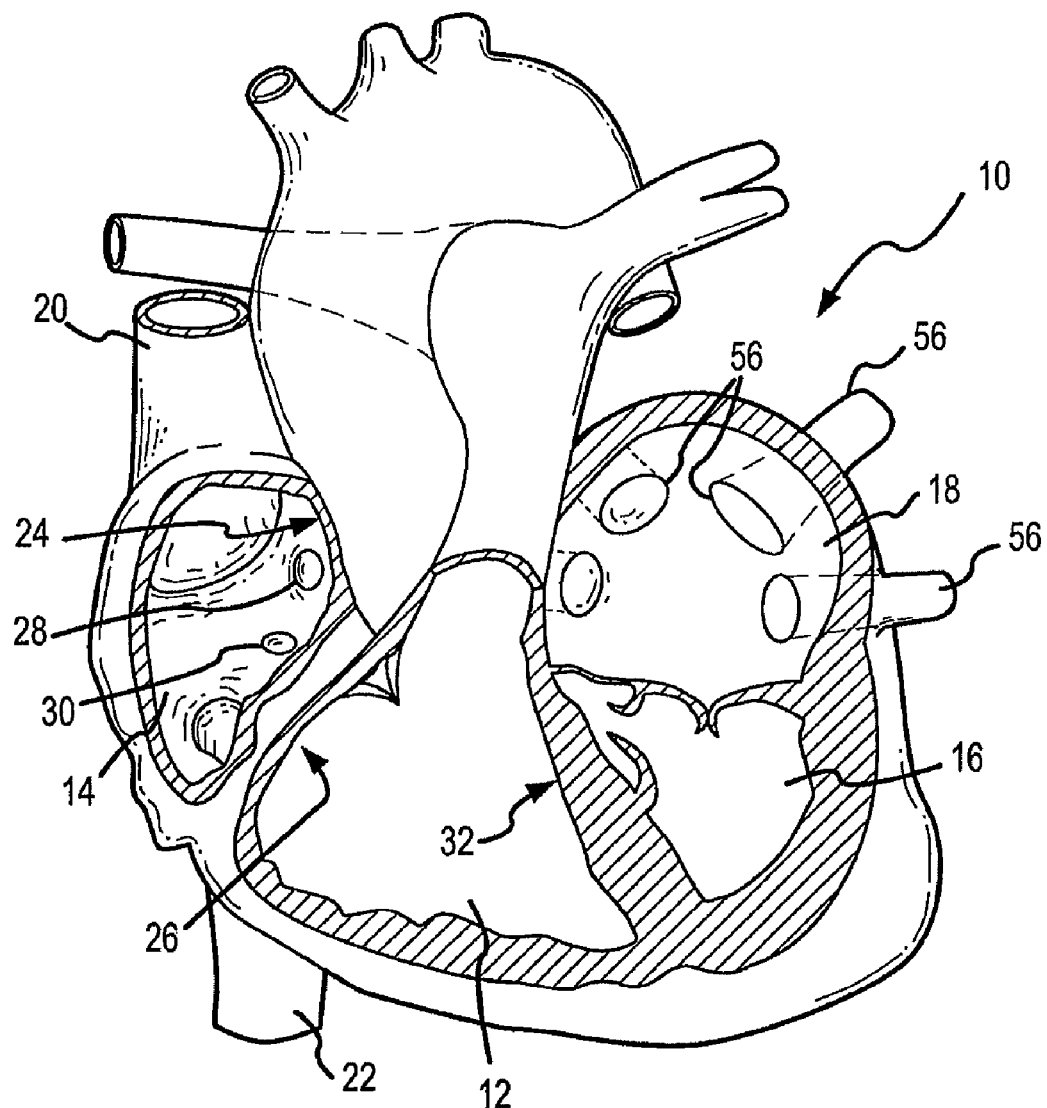
FIG. 1 is a partial cut away front isometric view of a human heart.

One aspect of the present invention involves a medical device, such as a catheter or pacemaker lead, employing a flexible printed circuit adapted to convey signals and energy along some portion of the medical device. In one particular implementation conforming to the invention, a catheter may be used for mapping or diagnostic purposes. In such an implementation, the catheter has a tubular body including a distal tip portion with the sensing electrodes and a proximal shaft. The flexible printed circuit acts as a kind of wire harness. The flexible printed circuit has conductive traces electrically connected with the sensing electrodes to convey bioelectric signals through the catheter to an electrocardiograph ("ECG"). The tip and shaft are of sufficient combined length to be routed through the vascular system of a patient to the location of tissue (i.e., "target tissue") that is going to be mapped. For example, to detect and map electrical signals in the left or right atrium, a catheter is oftentimes inserted into a patient at the femoral vein in the right leg, and routed up and into the patient's heart. Regardless of the location of the target tissue, while the catheter is routed to and from the target tissue, the catheter is oftentimes twisted, bent, and otherwise manipulated. The flexible printed circuit is able to twist and bend with the catheter.

As stated above, in one particular catheter implementation, the catheter includes one or more electrodes along its distal end region (or "tip") configured to receive bioelectric signals from target tissue. The electrodes may, however, be located at the device's distal end or anywhere along its length. One or more flexible printed circuits may be arranged to convey or transmit the bioelectric signals from the electrodes to a monitoring device directly or indirectly connected with or otherwise in communication with the flexible printed circuits. In one implementation, a connector, either directly or indirectly connected with the traces, is provided along the proximal end region of the catheter. The connector may be plugged into a corresponding connector for a monitoring device, such as the ECG.

As used herein and commonly used in the art, the term "distal" is used generally to refer to components of the catheter, such as the tip, that are located or generally orientated toward the heart or other target tissue when the catheter is in use. On the other hand, the term "proximal" refers to components or portions of the catheter, such as the connector, that are located or generally orientated away from or opposite the heart or target tissue when the catheter is in use. It should also be recognized, that something "proximally" located may be, at times, near the target tissue. For example, while the tip is at the distal end region of the catheter, the shaft, which is proximal to the tip, may have a certain portion that is, at times, in proximity to the target tissue.

Besides a diagnostic arrangement, a medical device conforming to aspects of the invention may be adapted to conduct energy or signals to a target tissue, such as conduction pacing signals, ablation energy, and defibrillation signals or energy via one or more flexible printed circuits alone or in combination with wires or other conductive elements. Moreover, a catheter conforming to aspects of the present invention may be employed in a combination of diagnostic and energy arrangements, where signals or energy are conducted from and to the target tissue.

In one particular implementation, a catheter employing a flexible printed circuit may be arranged to conduct ablation energy to a target tissue. Hereafter, the term "ablation energy" will be used to refer to any energy type used to ablate tissue, such as radio frequency (RF), direct current, alternating current, microwave, ultrasound, and ohmic. Generally, to convey ablation energy along the flexible printed circuit to a target tissue will require a larger trace dimension then is required to convey bioelectrical signals along the flexible printed circuit from the target tissue. Conductive trace width and spacing for a printed circuit is a function, at least in part, of the current capacity and voltage that is expected to be conveyed along the trace.

FIG. 2 illustrates a top view of one implementation of a flexible printed circuit 34 or flexible printed circuit board that may be employed in a medical device conforming to the present invention. The flexible printed circuit has a plurality of conductive traces 36 defined thereon. As used herein the term "flexible printed circuit" is intended to encompass any printed circuit or printed circuit board arrangement having at least one conductive trace or electrically active element deployed in a non-rigid arrangement, such as traces printed on a flexible substrate. The flexible printed circuit may include one or more electrically conductive traces or electrically active elements arranged in any pattern. Depending on a particular implementation of a medical device, the printed circuit may include single or multiple conductive and insulating layers. Plated or unplated access holes, vias, pads, connectors, solder joints, and other means to access, communicate with, or otherwise connect with the conductive traces or elements may be employed as required by any particular implementation of the present invention. FIG. 2B illustrates an alternative implementation of a flexible printed circuit 34 similar to that shown in FIG. 2. The flexible printed circuit of FIG. 2B includes a channel 35 around the distal terminal end of the trace 36. The channels allow the distal end of the trace to be bent in order to connect with an electrode.

Figure 3:
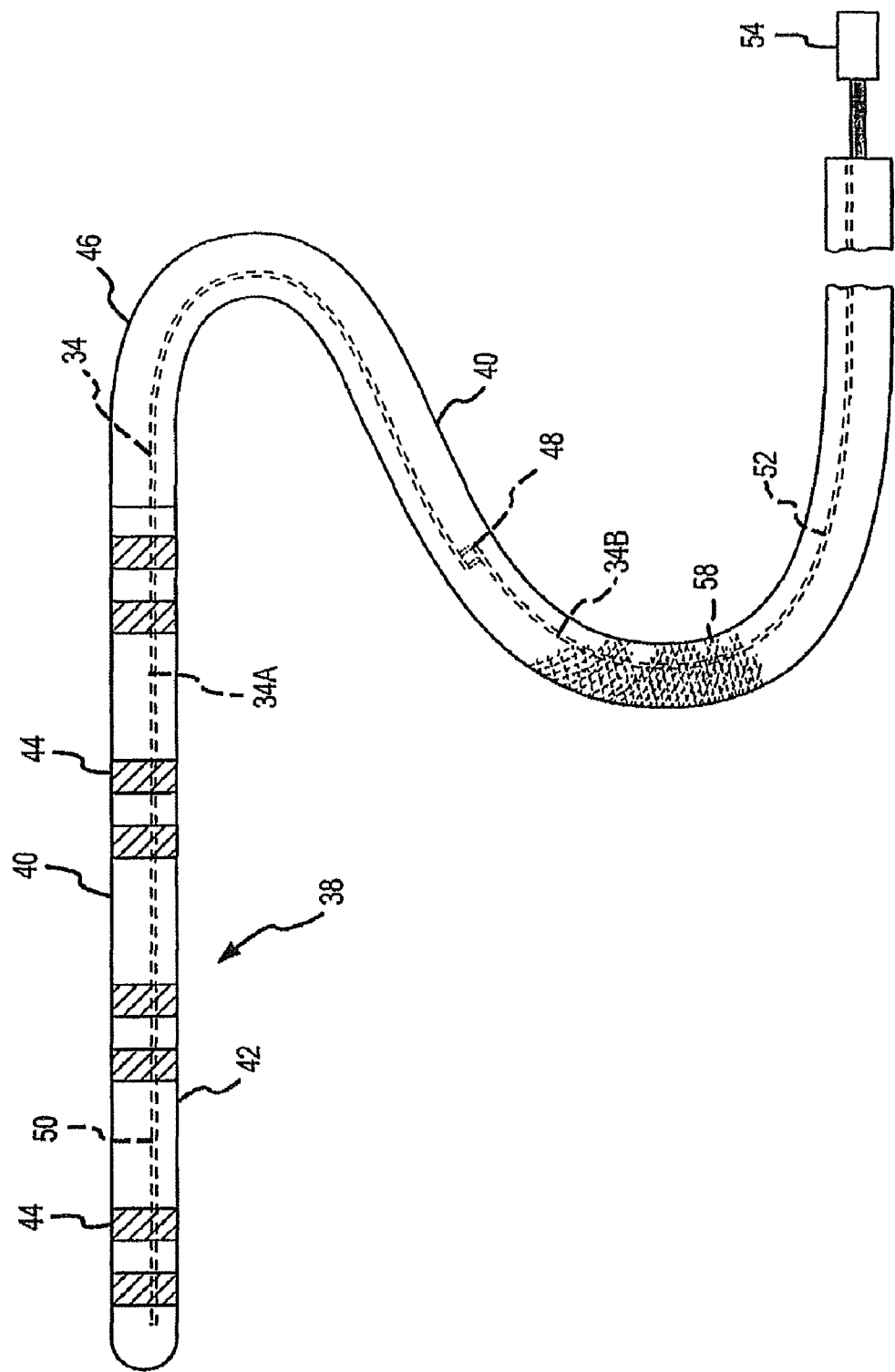
FIG. 3 is a top view of one implementation of a catheter employing a flexible printed circuit to convey signals to and from a target tissue, in accordance with the present invention.

FIG. 3 is a side view of one implementation of a catheter 38 employing a flexible printed circuit 34, in accordance with the present invention. The catheter generally has a tubular body 40, which may be flexible or include regions that are rigid. At the distal end region of the catheter, a tip region 42 includes at least one electrode 44 for receiving bioelectric signals from target tissue or conveying energy or signals to target tissue. Proximal to the tip, the catheter comprises a shaft 46. The tip region may be an extension of the shaft (i.e., integral with the shaft) or may be a separate piece connected to or otherwise bonded to the shaft. In some implementations, the catheter may be configured such that one or more of the electrodes are adapted to receive bioelectric signals and one or more of the electrodes are adapted to convey energy or signals. In the implementation shown in FIG. 3, a first flexible printed circuit 34A is employed along the distal portion of the catheter and a second printed circuit 34B is employed along the proximal portion of the catheter. The two flexible printed circuits are connected to each other at a connection point 48 using any conventional means of connecting printed circuits. The flexible printed circuits are situated within the shaft 46 and the tip portion 42. As will be discussed in further detail below, the shaft and tip may be molded to define an internal lumen adapted to receive one or more flexible printed circuits 34. Alternatively, the flexible printed circuits may be banded or otherwise adhered to all or a portion of the external surface of the shaft, located partially on the surface of the catheter and partially within a lumen, located partially or completely between tubular sub-layers of the catheter, or otherwise operably associated with the catheter.

The first printed circuit 34A is located in a lumen 50 defined in the tip. Along the distal region of the first printed circuit 34A, the traces 36 (not shown in FIG. 3) are connected with the various electrodes 44 situated along the tip 42 of the catheter. The proximal end of the first flexible printed circuit includes a connector or other means 48 by which the traces on the first flexible printed circuit may each be conductively connected with corresponding traces on the second flexible printed circuit 34B. One example of an adapter 48 is shown in FIG. 2A. The adapter on the first flexible printed circuit board, or tip board, has contact points at the terminations of each trace. The second flexible printed circuit board, or bridge board, also has contact points. Either the tip board or the bridge board have a latch that aligns the two boards and can clamp the boards together. The alignment system may consist of a pin and hole, tongue and grove, or snap fit edge. Alternatively the adapter could align the two boards and the boards could be pasted together. The second printed circuit 34B is located within the same lumen 50 or a similarly situated lumen 52 along the proximal portion of the catheter. In this implementation, the second flexible printed circuit terminates with a second connector 54 or adapter at its proximal end. The proximal end region of the second flexible printed circuit extends outwardly of the shaft 46 of the catheter. As such, the second adapter is located outside of the shaft. The adapter facilitates connection between the device and a diagnostic or energy-generating apparatus. The adapter or connector discussed herein generally may include embedded, conductive adapter traces or other conductive means, such as pins, wires, joints, and the like that may electrically connect the traces on the second printed circuit to leads or other conductive member on the diagnostic or energy generating apparatus. The adapter shape and particular implementation (as well as the shape and implementation of the portion of the adapter mating with the apparatus) may vary.

To guide the catheter 38 to target tissue, the catheter may be used alone or with guiding and introducing type devices and steering devices depending on the particular procedure being performed. As such, the shaft 46 and tip 42 may define additional communicating and non-communicating lumens. For example, an additional lumen may be adapted to house a pull wire or as a guide so that the catheter may be fed into the patient over a guide wire. In one implementation, the shaft and the tip are fabricated with a flexible resilient material so that they may flex while being manipulated and guided through the patient. Alternatively, the catheter may employ a "fixed curve" type tip.

A directional control mechanism of any type presently used may be placed inside the catheter's lumen. Generally, at the distal end of the catheter, the directional control assembly is attached to the catheter tip. A wire or directional guide is affixed to a steering mechanism located at or outside the proximal end of the catheter. The control assembly may be affixed to the catheter tip in a variety of manners, including solvent adhesion, sonic welding, co-extrusion, and so forth. Alternatively, the tip may be formed or extruded around the control assembly, after which the entire tip structure may be affixed to the shaft tube.

In yet another embodiment, the catheter may be provided with a fluid-steerable armature, such as that described in application Ser. No. 10/613,796, entitled "STEERABLE AND SHAPABLE CATHETER EMPLOYING FLUID FORCE" and filed on Jul. 2, 2003, the entirety of which is hereby incorporated by reference.

In one example of routing the catheter to a target tissue, a guiding introducer having a sheath with at least one lumen may be employed to provide a conduit by which the catheter is guided to the target tissue. To pre-position the introducer at the appropriate location in the heart, a dilator and a needle (not shown) are fitted within the lumen of the introducer. When the dilator and needle are within the lumen, the catheter is not within the lumen. Referring to the heart shown in FIG. 1, to provide a conduit to the left atrium 18, the introducer and the dilator are first inserted in the femoral vein in the groin area. The introducer and dilator are then maneuvered up to the inferior vena cava 22 and into the right atrium 14 (more specifically, the introducer and dilator are maneuvered to the superior vena cava, the needle is placed in the lumen and dragged from the superior vena cava into the right atrium and to the fossa). In what is typically referred to as a transseptal approach, the needle is pressed through the interatrial septum 24 via the fossa ovalis 28 between the right and left atrium. Following the needle, the dilator is pressed through the small opening made by the needle. The dilator expands the opening sufficiently so that the introducer may then be pressed through the opening to gain access to the left atrium 18 and perhaps the pulmonary veins 56, which may be a pathway for stray signals. With the sheath in position, the dilator and needle are removed and the catheter is fed into the lumen of the sheath and pushed along the sheath into the left atrium 18. When positioned in the left atrium, various procedures, such as mapping and ablation, may be performed therein. In some implementations, the introducer and the catheter 38 are each about two to four feet long, so that they may extend from the left atrium through the body and out of the femoral vein in the right leg and be connected with various diagnostic and ablation devices.

The shaft 46 and tip 42 are preferably fabricated of materials suitable for use in humans, such as nonconductive polymers. Suitable polymers include those well known in the art, such as polyurethanes, polyether-block amides, polyolefins, nylons, polytetrafluoroethylene, polyvinylidene fluoride, and fluorinated ethylene propylene polymers, and other conventional materials.

Referring again to FIG. 3, a portion of the catheter, such as a portion of the shaft 46, may include a braided material 58 to impart additional stiffness and/or structural strength. Wire of any suitable material may be braided into a portion of the shaft to stabilize and stiffen the catheter. For example, a portion of the device's exterior may be braided with a fiber such as Vectran™ or a wire such as stainless steel or nitinol, while a separate portion of the catheter may lack such braids in order to permit more ready flexing. The braids may form a cross-hatch pattern to facilitate stiffness. Generally, this braided wire does not conduct energy during catheter operation, and is not operably connected to a trace or electrode. Further, the braided wire 58 typically is embedded within the shaft 46 or tip 42, rather than placed along its surface where it may abrade tissue if inserted within a body. The braided wire may or may not be visible to the eye when the shaft surface is viewed. Accordingly, the braid 58 is shown in phantom (dashed lines) in FIG. 3.

FIG. 4 is a top view of the tip portion 42 of a catheter 38 employing a flexible printed circuit, in accordance with one implementation of the present invention. Note, in the various Figures, reference numbers are used to refer to like elements. FIG. 5 is a side view of the catheter tip illustrated in FIG. 4. As shown in FIG. 5, the flexible printed circuit 34 is located in a circuit lumen 50 arranged adjacent to a central lumen 60 along the longitudinal axis of the catheter. A lumen, generally speaking, is a tubular channel or open area running along some or all of the length of the catheter. Lumens are employed in diagnostic and other catheters for a variety of reasons, such as to convey liquids along the length of the catheter, to provide a conduit for guide wires, pull wires, electrically conductive wires, and stiffener wires such as Nitinol™, and for other purposes. In accordance with aspects of the present invention, a lumen (referred to herein as the "circuit lumen") may also be employed as a conduit for a flexible printed circuit. The lumen or lumens, including the circuit lumen, may be integrally formed or molded in the shaft and tip or may be a separate tube located, integrated, or molded within the shaft or tip. Embodiments of a catheter conforming to the present invention may include one or more lumens or may be implemented without a lumen. A flexible printed circuit may be housed in a lumen or molded directly within the tip or shaft.

The catheter tip portion 42 may be fabricated from a number of materials or material combinations, depending on the desired function of the catheter. The catheter tip may include one or more electrodes 44, or may be entirely covered by a single electrode, when the catheter tip 42 is used for diagnostic or ablative purposes. Alternatively, where such functions are unnecessary, the catheter tip may be formed from a nonconductive material, such as that used to form the shaft 46, or may be simply metal-plated with no operable connection to any trace, wire, or electrode. Further, if a medical device such as a guide wire is passed through the catheter, the tip may have an opening at its end, regardless of the material used to construct the tip. In some implementations, the flexible printed circuit board 34 may be made of biocompatible materials such that the board itself can be used as the final catheter or lead.

In an alternative embodiment, the tip 42 may include radiopaque material to permit detection of the tip during fluoroscopy or related procedures. The radiopaque material may be bonded to the inside or outside of the catheter, along the lumen 60, or may be embedded within the catheter walls. The tip may also be formed with radiopaque material. Further, the radiopaque material may be suspended within a polymer, or may be one or more solid, contiguous pieces of material. For example, the radiopaque material may take the form of fine particles suspended in a polymer tube, or may be a ring of radiopaque substance bonded to the inner surface of the jacket or tube. Exemplary radiopaque materials suitable for use with the present invention include metals such as platinum, tungsten, gold, or other metals opaque to x-rays, or polymeric materials designed to be x-ray opaque.

In the implementation of FIGS. 4 and 5, a plurality of ring-shaped electrodes 44 are circumferentially positioned along the tip 42. The electrodes are generally arranged such that the outer surface of electrodes are roughly level with the adjacent outer surface of the tip. As such, an electrode may be slightly raised, slightly lowered, or evenly aligned with the adjacent outer surface of the tip. In the catheter shown in FIGS. 4 and 5, the electrodes are arranged in four pairs (62A, 62B, 62C, and 62D). The electrodes in each pair are separated by about 2 mm, and each pair of electrodes is separated from an adjacent pair by 5 mm. Other arrangements and numbers of electrodes may be employed, such as electrodes separated by 5 mm or 10 mm, and having anywhere from 1 to 20 electrodes along the tip. The present invention is not limited to any particular number, location, or configuration of electrodes. Moreover, the present invention is not limited to any particular shape or configuration of electrode.

Figure 6:
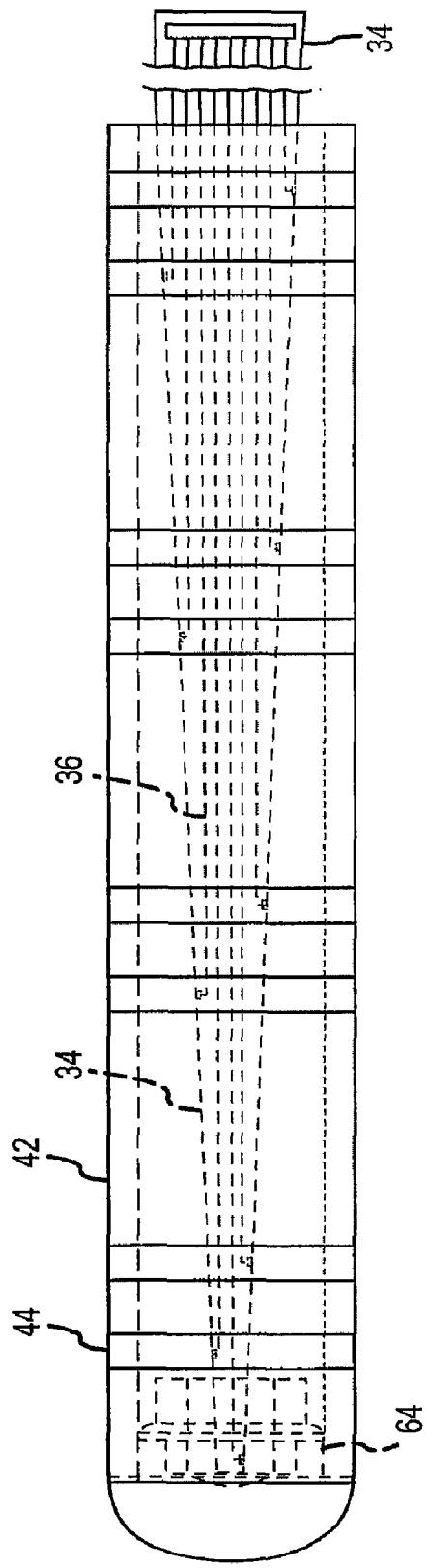
FIG. 6 is a partial top view of a distal tip region of an alternative implementation of a catheter showing a flexible printed circuit in a hidden line, the catheter of FIG. 6 including a tip electrode.
Figure 7:
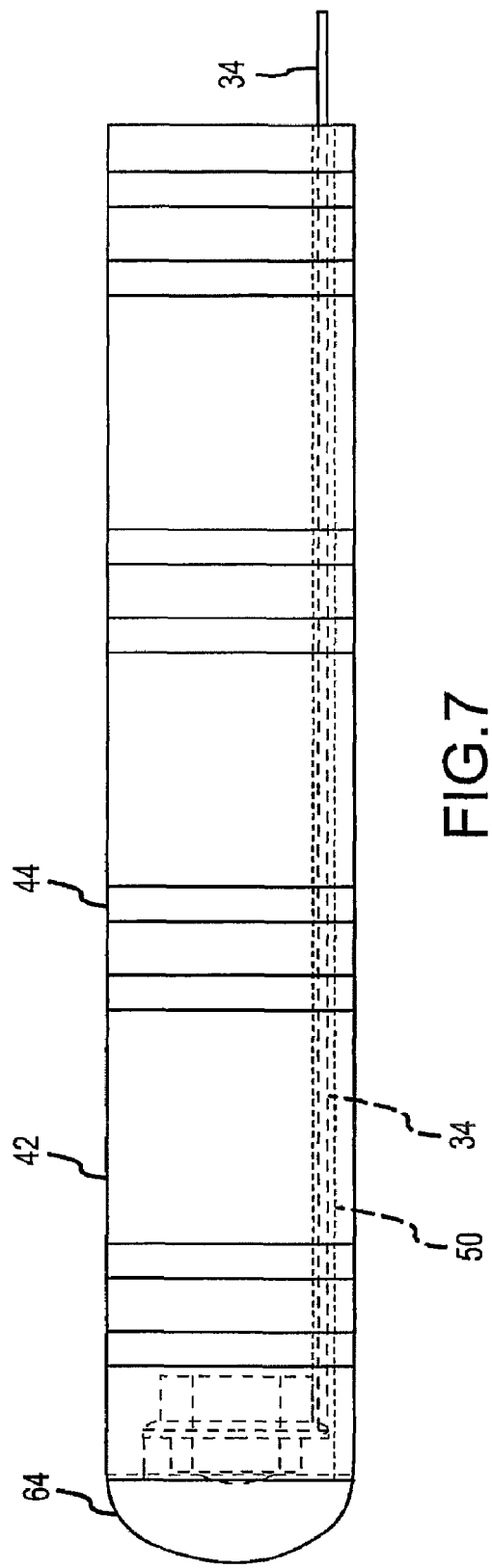
FIG. 7 is a partial side view of the catheter of FIG. 6.

FIG. 6 is a top view of an alternative catheter 38 employing a flexible printed circuit 34, in accordance with the present invention. FIG. 7 is a side view of the catheter shown in FIG. 6. The catheter shown in FIGS. 6 and 7 is similar to the catheter shown in FIGS. 4 and 5. However, unlike the implementation of FIGS. 4 and 5, the implementation of FIGS. 6 and 7 does not include a central lumen 60 and does include a tip electrode 64. A trace 36 of the flexible printed circuit may be connected with the tip electrode. Moreover, the catheter may be configured such that the tip electrode is used to receive bioelectric signals transmit ablation energy, or is electrically inactive.

In one particular arrangement, the tip electrode 64 is configured as a conduit for ablation energy to be transmitted to a target tissue, and the ring electrodes 44 are configured to receive bioelectric signals. In such an arrangement, the trace connected with the tip electrode will likely have a greater overall dimension than the traces connected with the ring electrode. One advantage of such an arrangement is that both diagnostic and ablation procedures may be performed with a single catheter.

A catheter conforming to aspects of the invention may also be fitted with other electrical elements, such as temperature sensing elements. For example, a thermistor may be embedded or otherwise incorporated into the shaft 46 or tip portion 42 of the catheter 38. The thermistor leads (in the case of a chip-style thermistor) may be attached to or in communication with one or more traces in order to accurately convey temperature readings to an associated monitoring device in communication with the catheter. The thermistor may be located beneath or adjacent to an ablation electrode in order to measure the electrode temperature during ablation. The thermistor may, for example, be placed in a depression in the tubular surface of the tip and covered with a relatively thin layer of nonconductive material (but heat conductive) to prevent electrical interference. An electrode may then rest above the thermistor, at least partially within the same depression and connected to a trace 36 other than that operably connected to the thermistor. In this manner, the thermistor may measure the operating temperature of the electrode without interfering with the electrode's operation.

In yet another alternative embodiment, the thermistor may be replaced by a thermocouple. Again, an electrode may be placed or formed within the depression and the thermocouple may measure the temperature generated by the electrode to assist, for example, in monitoring tissue temperature experienced during ablation. If necessary, an electrically nonconductive (but heat conductive) layer may separate the thermocouple junction and electrode. Such a layer generally will withstand the temperature generated by the electrode without deforming, warping, or suffering performance impairment.

The thermistor is a circuit element coupled to the flexible printed circuit 34. Other circuit elements may be attached to or in communication with the flexible printed circuit 34 on the internal side. Examples of such circuit elements include measurement circuitry, therapy delivery circuitry, and active circuits such as multiplexers.

In the diagnostic catheter implementations shown in FIGS. 4-7, the distal end of each trace 36 on the flexible printed circuit 34 (see also FIG. 2) is in communication with a single ring electrode 44. As such, signals received from any particular electrode are conveyed to a corresponding trace of the flexible printed circuit. Some conventional flexible printed circuit manufacturing technology is limited to flexible printed circuits of about 2 feet, unless a spiral on the production sheet is employed. Thus, if a particular catheter implementation is longer than two feet, it may be necessary to provide additional electrical signal conveying means connected with the traces on the flexible printed circuit. The proximal ends of the traces may thus be connected with traces of one or more additional flexible printed circuits such as is shown in FIG. 3. The proximal ends of the traces may also be connected with wires or connected with other electrically conductive arrangements or signal conveying means. At the distal end of the catheter, the signals received from the electrodes are communicated to diagnostic and/or recording equipment so that the signals may be analyzed.

Figure 8:
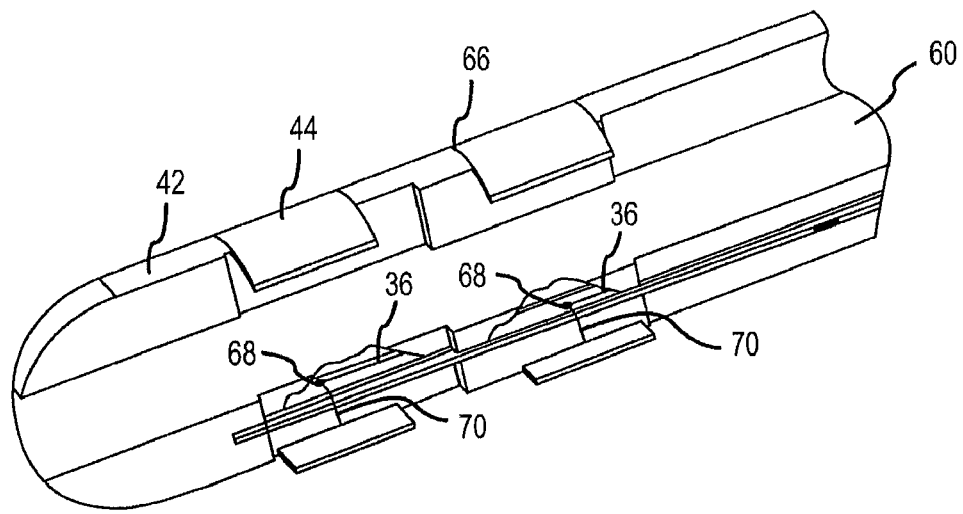
FIG. 8 is a partial cut away isometric view of one implementation of a catheter employing a flexible printed circuit to convey signals to and from a target tissue, in accordance with the present invention.

Referring to FIG. 8, a close-up partial isometric section view of the tip portion of the catheter of FIGS. 4 and 5 is shown. In this view it can be seen, that the tip 42 is formed with slight circumferential depressions 66 adapted to receive the electrode rings 44. However, it is not necessary to include a depression for a ring electrode. The electrode rings are in-molded, pressed, glued, swaged, or otherwise connected with the catheter 38 at the corresponding depressions. The flexible printed circuit 34 is arranged generally parallel with the longitudinal centerline of the catheter. It can further be seen, that each trace 36 is printed such that when it is properly positioned in the catheter, the distal ends end 68 of the trace is located in alignment with a corresponding electrode. In the arrangement shown in FIG. 8, a connection 68 is formed between the electrode and a corresponding trace on the flexible printed circuit. The connection may be accomplished with a via, solder joint, solder paste or the like, forming an electrical path between the electrode and the trace. The connection may also be formed with a wire extending between the proximal end region of a trace on the flexible printed circuit and the corresponding electrode. This connection permits the trace to pass electrical energy from a monitoring device affixed to the outside of the catheter at its proximal end to the electrode, or vice versa. The trace may be offset either along the longitudinal or lateral axes of the catheter from the electrode, so long as some portion of the trace remains in contact with the electrode.

Further, the geometry of a trace and electrode may vary widely. For example, the electrode may be fully or partially cylindrical, forming a ring extending partially or entirely around the circumference of the tip. Regardless of electrode shape, the trace typically runs along the longitudinal axis of the printed circuit at least to the edge of the electrode. The trace may also have any cross-sectional shape desired. Accordingly, the cross-sections of both the electrode and trace may vary in both a lateral and longitudinal cross-section, as may the depth or thickness of the trace and electrode.

In the present embodiment, each trace typically electrically connects to a single electrode. In this manner, discrete electrical signals are communicated between the electrode and any apparatus attached to the proximal end of the trace, minimizing or eliminating signal interference or cross-talk. If an apparatus controls or employs multiple sensory points with a single trace, then the trace in question may contact multiple electrodes.

Figure 9:
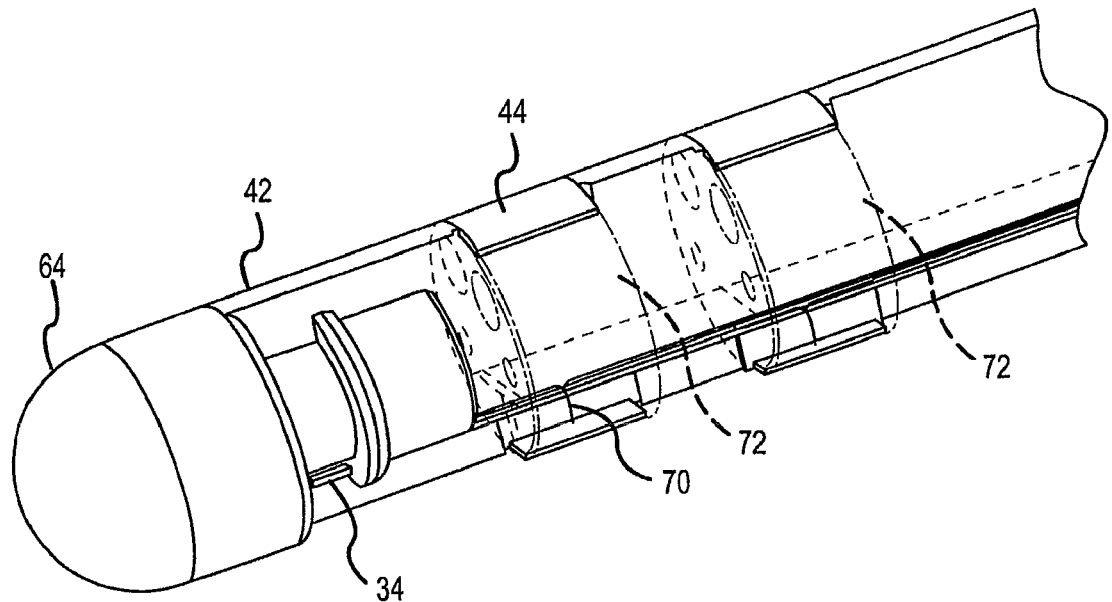
FIG. 9 is a partial cut away isometric view of an alternative implementation of a catheter employing a flexible printed circuit and including a tip electrode, in accordance with the present invention.
Figure 11:
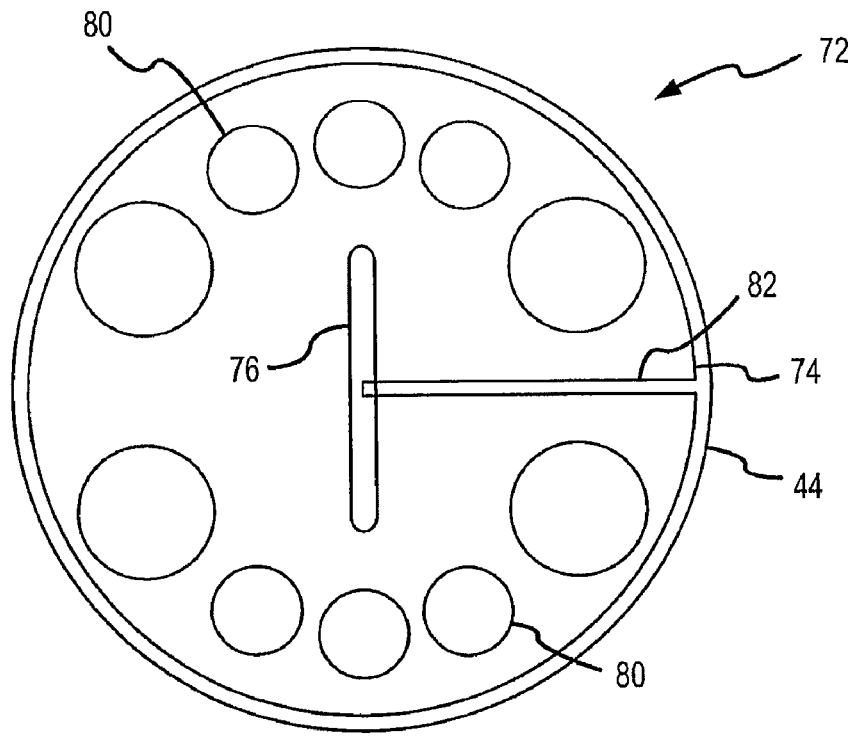
FIG. 11 is a front view of the spacer shown in FIG. 10.
Figure 10:
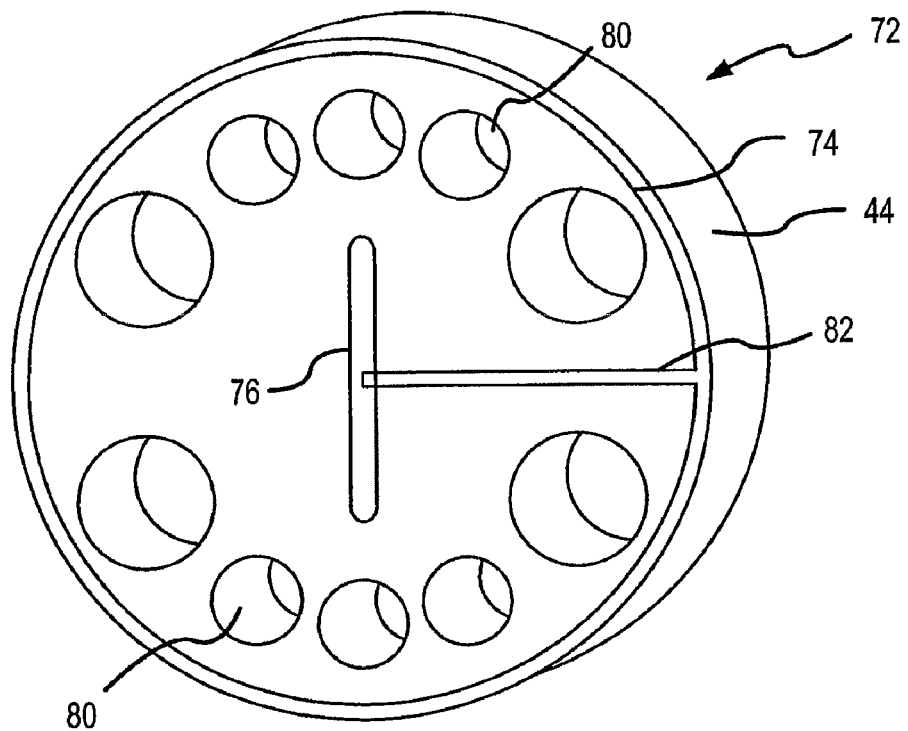
FIG. 10 is an isometric view of one implementation of a spacer or assembly aid for use in manufacturing a catheter employing a flexible printed circuit board, in accordance with the present invention.
Figure 13:
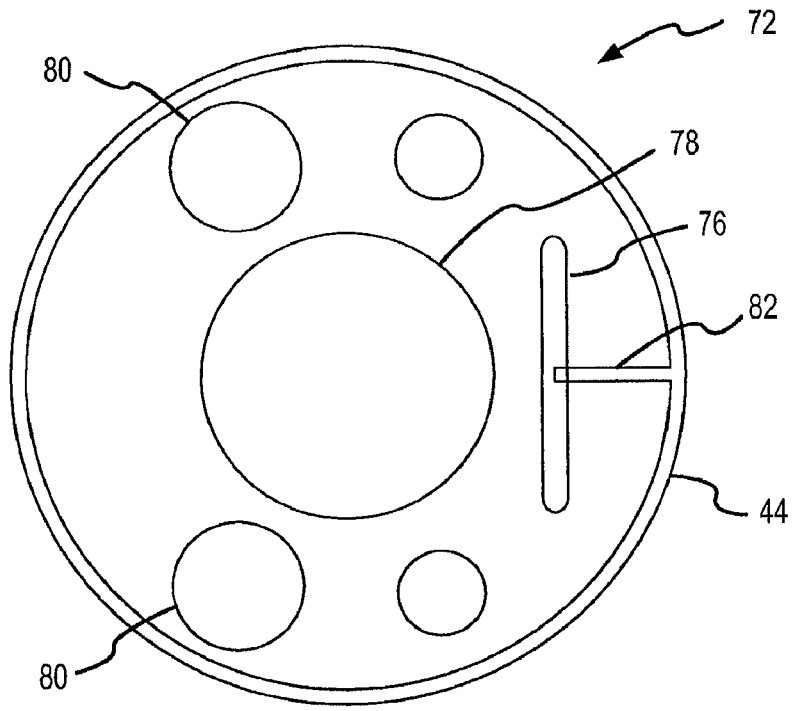
FIG. 13 is a front view of the spacer shown in FIG. 12.
Figure 12:
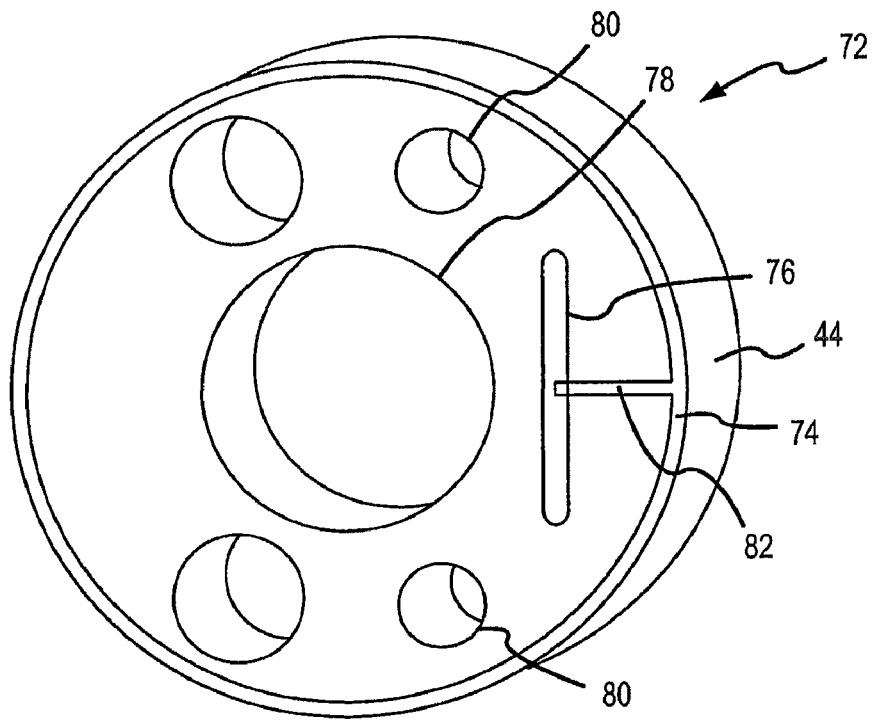
FIG. 12 is an isometric view of an alternative implementation of a spacer or assembly aid for use in manufacturing a catheter having a central longitudinal lumen and employing a flexible printed circuit board, in accordance with the present invention.
Figure 16:
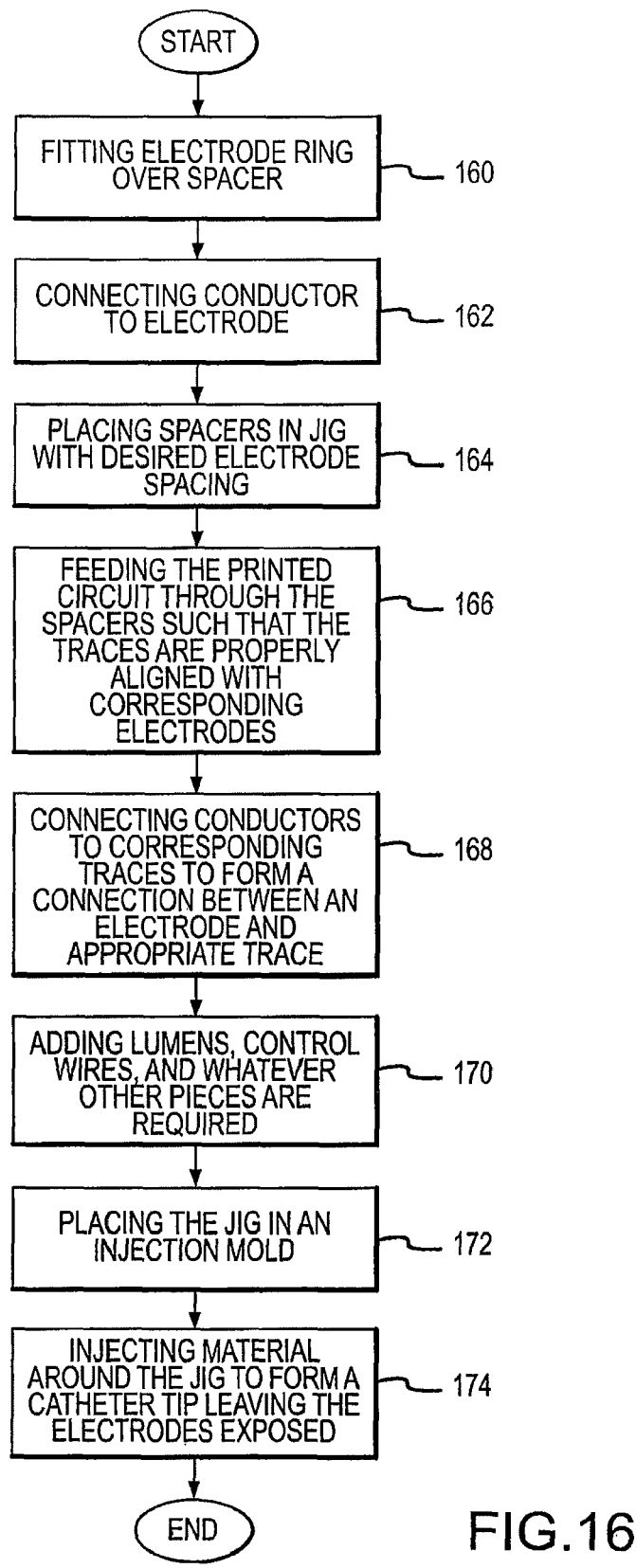
FIG. 16 is a flowchart illustrating the operations involved in one method of manufacturing a catheter employing a flexible printed circuit, in accordance with the present invention.

FIG. 10 is an isometric view of a spacer 72 used in one particular implementation of a catheter and associated manufacturing method involving injection molding for producing a catheter tip, such as is shown in FIGS. 6 and 7. FIG. 11 is a front view of the spacer 72 shown in FIG. 10. FIG. 9 is a close partial isometric section view of a catheter employing the spacer of FIGS. 10 and 11 (shown in hidden line). FIG. 12 is an isometric view of an alternative spacer 72 used in one particular implementation of a catheter and associated manufacturing method involving injection molding for producing a catheter tip, such as is shown in FIGS. 4 and 5. FIG. 13 is a front view of the spacer shown in FIG. 12. FIG. 16 (discussed further below) is a flowchart of one particular implementation of a manufacturing method for producing a catheter tip using a spacer, in accordance with the present invention.

Generally speaking, injection molding involves the injection of a material, such as the various polymers identified above heated to a fluid state, into a mold defining the shape of the catheter. Typically, an injection mold has an upper half and a lower half. The upper half of the mold defines a cavity corresponding to a surface of the part being molded and the lower half of the mold also corresponds with a surface of the part being molded. When the mold is closed, the upper and lower cavities of the mold are aligned such that together they define the part to be molded. The mold also includes a series of injection ports through which the fluid polymer is injected into the cavity to form the part. When the polymer has cooled and solidified, the mold is opened and the molded part is removed.

Figure 15:
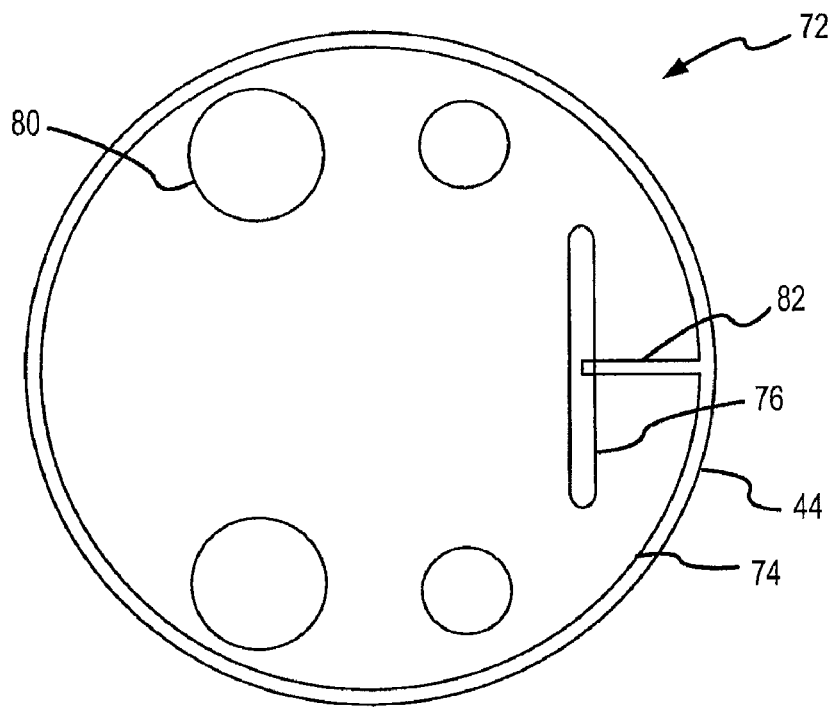
FIG. 15 is a front view of the spacer shown in FIG. 14.
Figure 14:
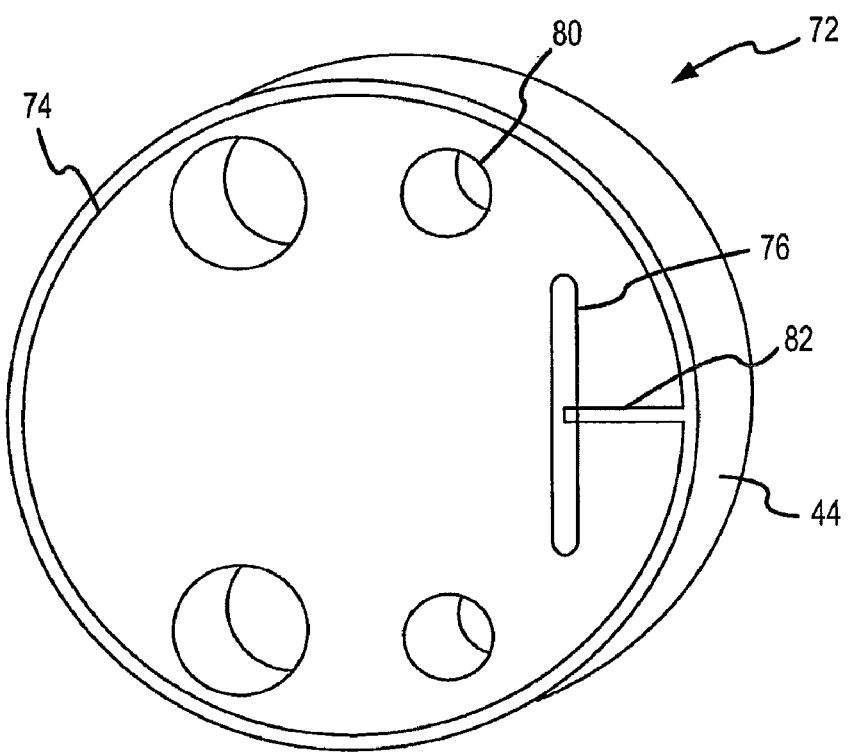
FIG. 14 is an isometric view of an alternative implementation of a spacer or assembly aid for use in manufacturing a catheter employing a flexible printed circuit board, in accordance with the present invention.

With reference to FIGS. 10-13, the spacer 72 defines a cylindrical main body 74. An elongate printed circuit aperture 76 is formed in the spacer. The elongate aperture is adapted to receive and locate the flexible printed circuit 34 during assembly. In FIGS. 10 and 11, the printed circuit aperture is shown arranged about the longitudinal centerline of the spacer. FIGS. 14 and 15 illustrate an isometric view and front view, respectively, of a similar spacer having the printed circuit aperture 76 arranged offset from the longitudinal centerline of the spacer. The spacer shown in FIGS. 14 and 15 is used to form the catheter tip shown in FIGS. 6 and 7. In FIGS. 12 and 13, the printed circuit aperture is shown arranged parallel, but offset from, the longitudinal centerline of the spacer. The spacer of FIGS. 12 and 13 also defines a larger circular aperture 78 arranged along the longitudinal centerline of the spacer. The central circular aperture is adapted to receive tubular member during assembly to form the central lumen 60 as shown in FIGS. 4 and 5.

Although shown as an elongated generally rectangular aperture, the printed circuit aperture 76 may take on any desired shape to facilitate receipt of any shape printed circuit, and may be located at other portions of the spacer. In addition to the printed circuit aperture, a series of molding apertures 80 of differing circumferences are defined along the spacer 72 adjacent the outside circumference of the spacer. As will be described in more detail below, these apertures are adapted to allow injection molding fluid to flow through the apertures during formation of a catheter tip. Although shown defining a generally circular cylinder, the molding apertures 80 may be of any size or shape depending on a particular implementation, injection material being used, injection port arrangement, etc. In addition, some of the molding apertures 80 may be utilized instead to house or otherwise support one or more lumens, such as for guide wires, pull wires, stiffener wires, and the like, that may be necessary for various possible catheter implementations.

Referring now to the manufacturing method illustrated in FIG. 16, the spacers 72 shown in FIGS. 10-13 show a ring electrode 44 circumferentially connected with the outside surface of the spacer. The ring electrode (or the shaped electrode) may be clamped onto the spacer, swaged, or glued to the spacer 72 (operation 160). Additionally, the ring electrode may be fabricated with a recess or protrusion adapted to snap onto a corresponding protrusion or recess, respectively, defined on the spacer. Other electrode shapes and sizes may be connected with the spacer. Alternatively, the spacer may be fabricated partially or completely of conductive material. As such, the outside surface may serve as the electrode surface and the operation of fixing the electrode on the spacer would not be required.

Once the electrode 44 is coupled with the spacer 72, a conductor 70, such as short wire, is connected to the electrode and routed to the printed circuit aperture (operation 162). The wire may be soldered to the electrode. In one particular implementation, the spacer 72 defines a connector aperture 82 between the outer surface 74 of the spacer and the printed circuit aperture 76. A wire or other connection is then located within this aperture. Other suitable conductors may be used. For example, solder may be injected into the aperture to form a conductive solder line between the electrode and the printed circuit aperture. In another example, solder paste may be positioned in the aperture. The solder paste may be adapted to melt and flow during the molding process or in a separate operation to form a connection between the trace and the electrode. In the case of a spacer with an integral electrode (i.e., a spacer formed at least partially of a conductor), the conductive portion of the spacer body may be electrically connected with the appropriate trace.

The spacer 72 and electrode 44 are next placed into a jig or other fixture (operation 164). In implementations with multiple electrodes, the fixture is configured to receive a plurality of spacers with electrodes and to hold the spacers so that the electrodes are arranged with the appropriate spacing (e.g., 2 mm spacing between electrodes forming a pair and 5 mm spacing between electrode pairs). Once properly placed in the fixture, the flexible printed circuit 34 is routed through the printed circuit apertures 76 of each spacer (operation 166). The various traces 36 on the flexible printed circuit are each aligned with the appropriate electrode 44. To facilitate the proper positioning of the flexible printed circuit, the jig may include a stop block such that the distal end of the printed circuit engages the stop block. When in engagement with the stop, the distal ends 68 of the traces will be properly aligned with corresponding spacers. Other alignment methods and configurations are also possible.

Once the flexible printed circuit is properly positioned in the printed circuit apertures of the spacers, each trace is electrically connected with the corresponding electrode (operation 168) or each trace is directly connected to the spacer. In one particular implementation, the conductor already present in the spacer is soldered to the appropriate trace. Alternatively, the solder paste is heated to form a conductive path between the electrode and the trace (this operation may also be performed during the molding process). Next, tubular members meant to define a central lumen 60 or other lumen to house control wires, pull wires, and the like may be arranged in the appropriate spacer lumen 78 or 80 (operation 170). The control and pull wires may then be routed through the tubular member.

When the jig is properly fitted with spacers, the printed circuit, lumens, and the like, and all the proper connections between the electrodes and printed circuit traces are complete, the jig is placed in an injection mold (operation 172). The injection mold will define two mating cavities defining the final shape of the desired catheter tip, e.g., the catheter tips 42 of FIGS. 4-7. The catheter tips may be formed straight or with a curve, and may have various diameters, e.g., 4 French to 7 French.

When the jig is properly positioned in the mold, the mold is closed and fluid polymer material is injected into the mold to form the catheter (operation 174). The fluid material flows into the mold and through the apertures 80 along the outside circumference of the spacers 72. As such, the fluid fills in around the spacers and forms the catheter shape. The outer circumference of the electrode should mate with the walls of the mold cavity such that when fluid polymer material is injected into the mold, the electrode surfaces are not covered by the fluid polymer material. The spacer is fabricated of a non-conductive polymer suitable for use in humans, similar or the same as any of the polymers discussed above. In one particular method of manufacture, it is appropriate to use a polymer for the spacer with a melting temperature greater than the temperature of the fluid polymer material that will be injected into the mold during formation of the catheter tip. This helps to ensure that the integrity of the overall tip is maintained during the molding process.

When the fluid polymer material is cooled so that the catheter tip 42 is in solid form, the catheter tip is removed from the mold. In some instances, the molded tip will have defined a slightly raised ridge, referred to as "flash," at the location associated where the two halves of the mold meet. The flash material is removed so that the outside surface of the catheter tip is smooth. When removed from the mold, the catheter tip includes the electrodes 44 and the printed circuit 34 and the connections 70 between the electrodes and the traces 36 on the printed circuit.

To form a catheter, the tip 42 is glued, RF bonded, melted, or otherwise connected with the shaft 46. The flexible printed circuit 34 of the tip is connected with a wire harness, individual wires, a second printed circuit (e.g., printed circuit 34 B of FIG. 3), or other signal conveying means associated with the shaft. This step is typically performed before the shaft is bonded to the tip. As discussed above, the proximal end of the signal conveying means associated with the shaft may include a connector 48 adapted to connect with a diagnostic device, an ablation energy delivery device or the like. Alternatively, depending on the length of the completed catheter, the flexible printed circuit 34 of the tip portion 42 may be of sufficient length to traverse the length of the shaft 46. As such, additional signal or energy conveying means may not be required. The proximal end of the flexible printed circuit is fitted with a connector or otherwise provide with a way to electrically connect with diagnostic or ablation energy delivery equipment. The shaft may be integrally formed with the tip (which may not require a bonding operation) or may be separately extruded or molded and bonded to the tip.

Figure 17:
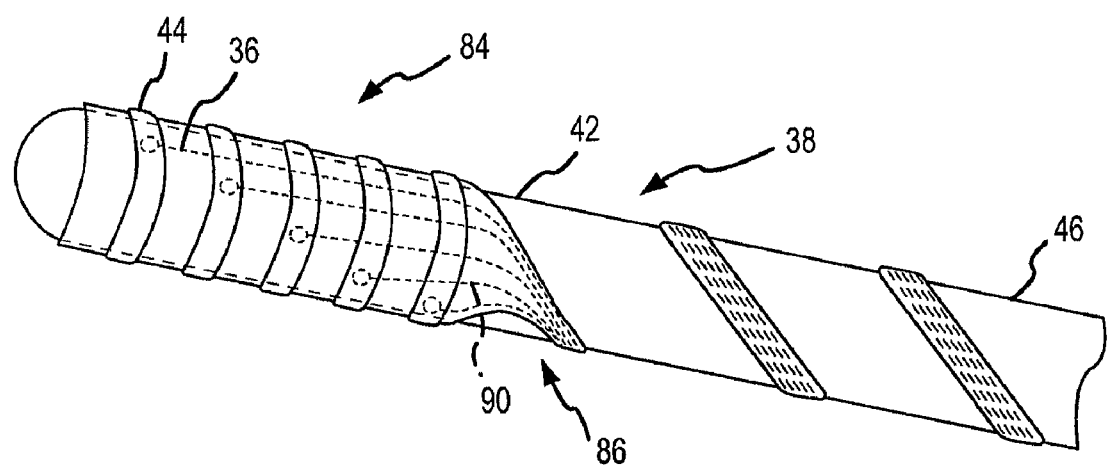
FIG. 17 is a partial isometric view of a catheter employing a flexible printed circuit secured in a helical manner near or along the outside of the catheter, in accordance with the present invention.

FIG. 17 is an isometric view of a catheter employing a flexible printed circuit 34 adhered to the outer surface of the tip 42 in a helical arrangement, in accordance with one implementation of the present invention. FIG. 18 is a top view of the flexible printed circuit of FIG. 17 before it is adhered to the outer surface of the tip. The flexible printed circuit shown in FIG. 18 defines a generally "flyswatter" like shape with a wide portion 84 and an elongate narrow portion 86. Along the wide portion, the flexible printed circuit includes a series of vertical traces 88 arranged generally parallel to each other. Each vertical trace, is adapted to be connected with a corresponding electrode 44. As such, the vertical traces are arranged in the desired electrode pattern (e.g., with 2 mm spacing between a pair of traces and 5 mm spacing between traces, with 5 mm spacing between each trace, etc.). Each vertical trace is electrically coupled with a corresponding horizontal trace 90. The horizontal traces are printed along the longitudinal portion of the printed circuit. As such, the horizontal traces are located on both the wide portion 84 and the narrow portion 86 of the flexible printed circuit 34 FIG. 17 is an isometric view of a catheter employing a flexible printed circuit 34 adhered to the outer surface of the tip 42 in a helical arrangement, in accordance with one implementation of the present invention. FIG. 18 is a top view of the flexible printed circuit of FIG. 17 before it is adhered to the outer surface of the tip. The flexible printed circuit shown in FIG. 18 defines a generally "flyswatter" like shape with a wide portion 84 and an elongate narrow portion 86. Along the wide portion, the flexible printed circuit includes a series of vertical traces 88 arranged generally parallel to each other. Each vertical trace, is adapted to be connected with a corresponding electrode 44. As such, the vertical traces are arranged in the desired electrode pattern (e.g., with 2 mm spacing between a pair of traces and 5 mm spacing between traces, with 5 mm spacing between each trace, etc.). Each vertical trace is electrically coupled with a corresponding horizontal trace 90. The horizontal traces are printed along the longitudinal portion of the printed circuit. As such, the horizontal traces are located on both the wide portion 84 and the narrow portion 86 of the flexible printed circuit 34.

The horizontal traces 90 and vertical traces 88 may be located on different layers of the printed circuit. In such an arrangement, the conductive layers may be separated by insulating layers. The horizontal traces on one layer and the vertical traces on another layer may be connected by vias (conventional, blind, buried, tented, etc.), through holes (plated or unplated) or other suitable interconnection means.

The flexible printed circuit shown in FIG. 19 is generally rectangular, and does not define a flyswatter like pattern. Otherwise, the flexible printed circuit of FIG. 19 is similar to the flexible printed circuit of FIG. 18. For example, the flexible printed circuit 34 includes a plurality of vertical 88 and horizontal 90 traces interconnected so that each vertical trace is connected with a corresponding horizontal trace. The traces may be located on the same layer or on separate layers, and the traces may be interconnected with vias, holes, and the like.

The flexible printed circuit boards illustrated in FIGS. 18-19 are adapted, in some implementations, to be disposed on the exterior of the tubular body 40 or tip 42 rather than being disposed in a lumen 50 (such as in FIG. 3). As such, the width of a flexible printed circuit 34 adapted for an external arrangement may be wider than a flexible printed circuit adapted for use in a lumen. The additional width provides for greater surface area so that a greater number of traces may be printed on the substrate or so that greater dimensioned traces, such as for ablation energy traces, may be printed on the substrate.

Figure 20:
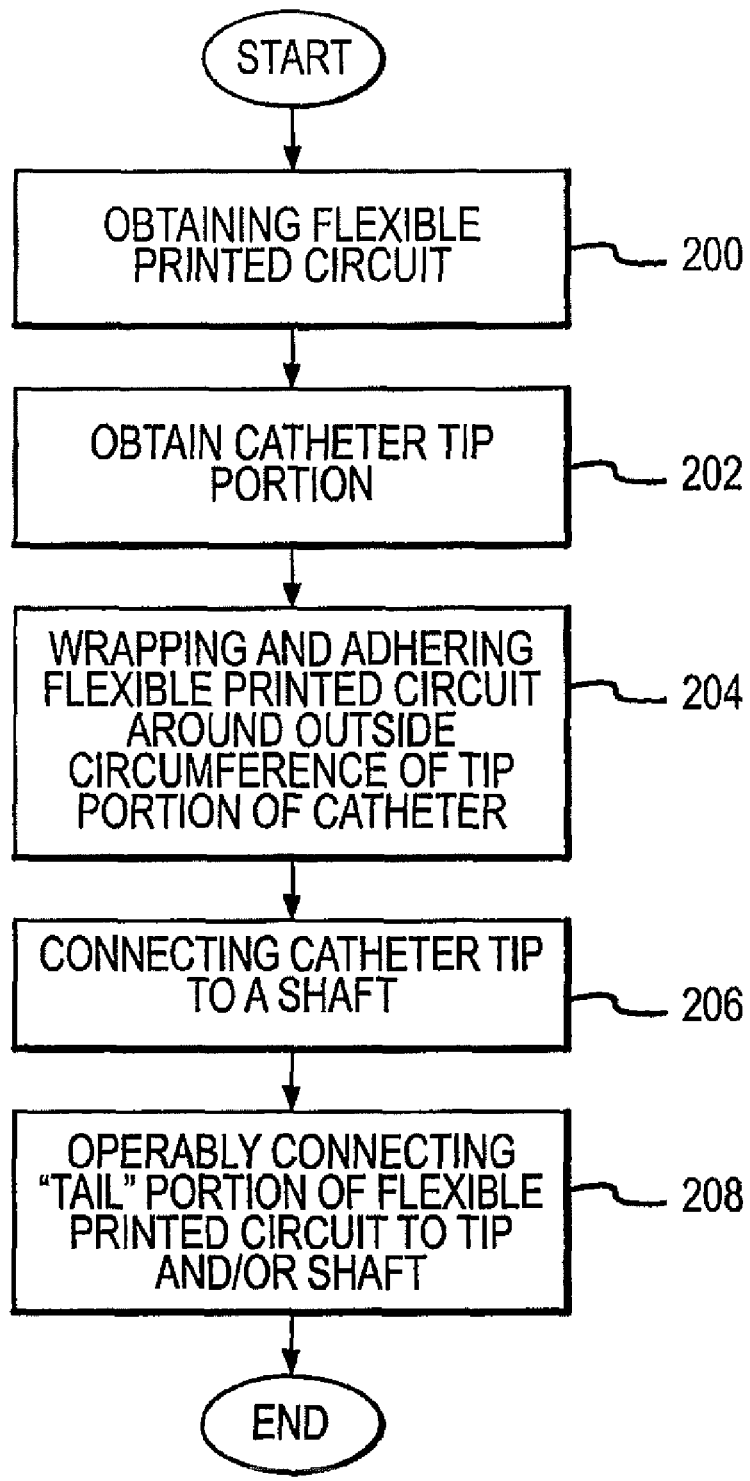
FIG. 20 is a flowchart illustrating the operations involved in one method of manufacturing a catheter employing a flexible printed circuit, in accordance with the present invention.
Figure 21:
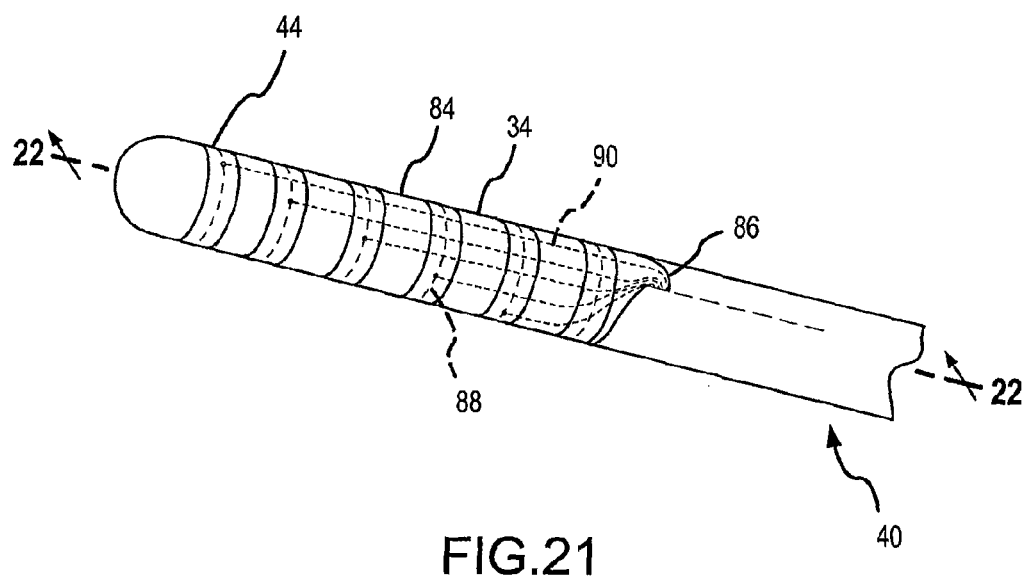
FIG. 21 is an isometric view of one implementation of a catheter employing a flexible printed circuit, in accordance with the present invention.

FIG. 20 is a flowchart illustrating one particular method of manufacturing a catheter employing a flexible printed circuit such as is shown in FIGS. 17 and 21 (discussed further below). First, an appropriate flexible printed circuit, such as is shown in FIG. 18 or FIG. 19, is obtained (operation 200) along with a tip portion 42 of a catheter (operation 202). The tip portion of the catheter may be formed through conventional extrusion or molding processes. The tip may or may not be curved, it may be form swaged, it may define one or more lumens, and it may include other characteristics.

Next, the flexible printed circuit 34 is wrapped around the outside circumference of the catheter tip 42 (operation 204). The flexible printed circuit may be glued, RF bonded, or otherwise adhered to the catheter tip. If the flyswatter shaped flexible printed circuit (FIG. 18) is used, then the wide portion 84 of the flyswatter is first bonded to the tip portion and the tail 86 or narrower portion is initially left loose. In a multi-layer printed circuit arrangement, the vertical traces 88 are preferably located on the outside of the printed circuit and the horizontal traces 90 are preferably located on the inside of the printed circuit adjacent the outside surface of the tip or tubular body or electrically isolated. After assembling the flexible printed circuit with the catheter tip, the vertical traces 88 form circumferential traces around the outside surface of the catheter tip. The horizontal traces are arranged generally longitudinally along the tip.

With the flexible printed circuit connected with the tip 42, the shaft 46 is next adhered to the tip (operation 206). Next, depending on the flexible printed circuit 34 employed, the flexible printed circuit is operably connected with the shaft. Referring to FIG. 17, an isometric view of the flexible printed circuit of FIG. 18 connected with a tip 42 and shaft 46 is shown. The tail portion 86 of the flexible printed circuit is helically or spirally wrapped around the shaft. Alternatively, the flexible printed circuit board may be fixed longitudinally to the shaft 46. The spiral wrap, however, provides somewhat greater flexibility to the overall shaft when the catheter is being bent or otherwise manipulated during a procedure. The tail portion may be bonded to the shaft. Additionally, a coating may be applied over the shaft and tail to hold the tail on the shaft and to smooth out the minor ridge between the flexible printed circuit and the shaft.

Figure 22:
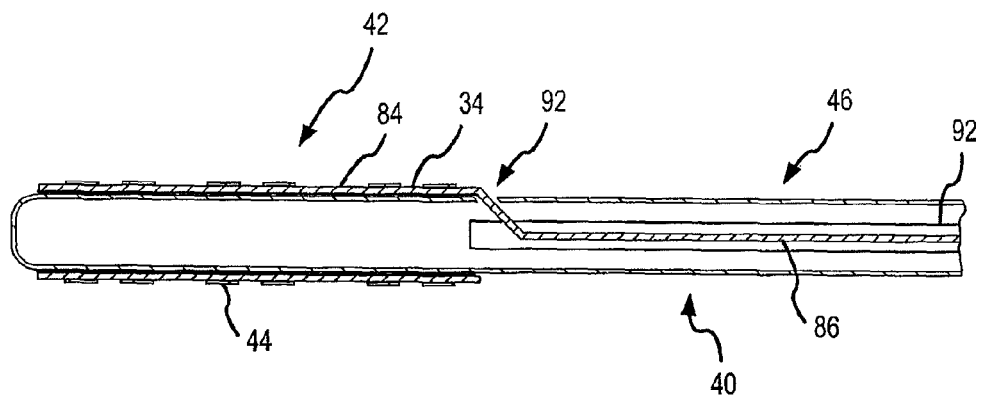
FIG. 22 is a section view taken along line 22-22 of FIG. 21.

Referring to FIG. 21, an isometric view of the flexible printed circuit of FIG. 18 connected with a tip 42 and shaft 46 is shown. FIG. 22 is a section view taken along line 22-22 of FIG. 21. Unlike the FIG. 17 embodiment, in this implementation, the tail portion 86 of the flexible printed circuit 34 is routed through an aperture 92 between the outside surface of the shaft and a lumen 92. As such, all or a portion of the tail is routed within the lumen of the shaft. The portion of the tail through the aperture may be bonded to the aperture or the aperture sealed so that fluid does not flow into the lumen via the aperture during use of the catheter.

Any of the printed circuits 34 shown herein may be initially manufactured such that multiple trace configurations are printed on a single substrate. Each separate trace configuration may then be cut from the single substrate for use in a medical device. In addition, the trace configurations may be printed so that they are scalable. For example, the flyswatter configuration may be initially printed with multiple pairs of vertical traces, each pair having traces separated by 2 mm and each pair being separated by 5 mm. The vertical pair may be trimmed off to form a flexible printed circuit with anywhere from one pair to five pairs of traces, for example.

As discussed herein, various implementations of the present invention include a catheter or lead employing a flexible printed circuit for conveying signals and/or energy. Each trace may be in electrical connection with one or more external electrical contacts or electrodes. More specifically, each trace is typically electrically connected to a single contact. The traces and contacts may assist in diagnosis and/or detection of bio-electrical signals emitted by organs, and may transmit such signals to a connector or diagnostic device in communication with the catheter. The external electrical contacts may detect bioelectric energy or may deliver electrical or thermal energy to a target site.

A catheter employing a printed circuit is also suitable for including other electronic elements or electrically active elements, such as an analog to digital converter, thermistor, transistors, integrated circuit configurations, crystals adapted for ultrasound ablation, and the like. Such a catheter may require multiple layers to implement the desired electrical element arrangement.

Any of the catheter embodiments described herein may also function as a device lead having electrodes (not shown). One exemplary function for such a lead is to regulate tissue contraction (for example, the beating of a human heart) by providing regularly timed electrical impulses. Generally, an embodiment of the present invention taking the form of a lead having a solid inner core or tube, insofar as few if any medical devices must pass through the lead itself. Alternative embodiments, however, may include communicating or non-communicating lumens running the length of the lead. Typically affixed to the lead is a pacemaker or other power source capable of providing electrical impulses at timed intervals. The lead may also incorporate a diagnostic electrode at or near the tip, to monitor the bioelectric impulses generated by the regulated tissue. In this manner, the lead may incorporate both the energy delivery or tissue regulating and diagnostic functions described herein. If a diagnostic function is provided, a discrete trace generally operably connects the diagnostic electrode to a diagnostic apparatus.

Although such electrical impulses may be delivered through any sufficiently conductive portion of the lead surface operably connected to a power source (such as a pacemaker), many leads are equipped with a tip or distal electrode. The location of the distal electrode at the end of the lead provides a simplified contact point for ensuring that the electrode is in contact with the tissue, insofar as a doctor or surgeon must maneuver only the tip of the lead into contact. In alternative embodiments, the tip electrode may be omitted and an electrode located along the lead sidewall may be used to deliver electrical impulses. The lead may be permanently implanted, or may be intended for temporary use by a patient.

A pacing or internal cardiac defibrillator lead is of sufficient length that it can connect the pacemaker or internal cardiac defibrillator from its permanent placement within the body of the patient to the desired lead electrode placement location on the heart. The pacing lead has one or more electrodes and may have one or multiple tips. For example a lead designed for use in chronic heart failure treatment may be bifurcated twice along the length of the lead such that the lead has three terminating ends each of which could have one or more electrodes. Each terminating end would be designed to be located in a specific location within the heart such as the left ventricle via the coronary sinus, the right ventricle, and the right atrium. The internal cardiac defibrillator lead has one or more electrodes and may have one or multiple terminating ends. One of the electrodes in the internal cardiac defibrillator lead will have a sufficient surface area that it can safely transmit cardioversion energy without risk of ablating tissue. The cardioversion electrode is generally placed in the apex of the right ventricle while the internal cardiac defibrillator implant (known as the "can") acts as the other electrode during cardioversion. Both pacing and internal cardiac defibrillator leads are flexible as they are located in a dynamic environment.

Although preferred embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, such joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A medical device for introduction into a human body comprising:
   a generally tubular body;
   a plurality of ring-shaped electrodes coupled with the tubular body, wherein the ring-shaped electrodes are arranged in at least two pairs, wherein a spacing separating the electrodes of a pair is less than a spacing separating adjacent pairs; and
   at least one printed circuit comprising a plurality of conductive traces in communication with the plurality of ring-shaped electrodes,
   wherein at least a portion of the at least one printed circuit is internal to the generally tubular body.

2. The medical device of claim 1 wherein the at least one printed circuit comprises at least one flexible printed circuit.

3. The medical device of claim 1 wherein the tubular body comprises at least one lumen housing at least a portion of the printed circuit.

4. The medical device of claim 1 wherein the tubular body defines a cylindrical outside surface and at least a portion of the printed circuit is coupled with the outside surface.

5. The medical device of claim 1 wherein the plurality of electrodes are adapted to receive signals from a target tissue.

6. The medical device of claim 1 wherein the plurality of electrodes are adapted to convey energy to a target tissue.

7. The medical device of claim 1 further comprising at least one wire in communication with at least one tip electrode.

8. The medical device of claim 1 wherein the plurality of conductive traces are in communication with a connector.

9. The medical device of claim 1 wherein the at least one printed circuit comprises a first printed circuit defining at least one first conductive trace and a second printed circuit defining at least one second conductive trace.

10. The medical device of claim 9 wherein the at least one first conductive trace is in communication with the at least one second conductive trace.

11. The medical device of claim 1 wherein at least one of the at least one conductive traces is adapted as the at least one electrode.

12. The medical device of claim 1 wherein the at least one printed circuit is coupled with the tubular shaft such that at least one of the conductive traces is at least partially circumferentially coupled with the tubular body.

13. The medical device of claim 1 further comprising a tip electrode.

14. The medical device of claim 1 wherein the tubular body defines a tip.

15. The medical device of claim 1 wherein the tubular body defines a shaft.

16. The medical device of claim 1 wherein the tubular body is flexible.

17. The medical device of claim 1 further comprising a steering mechanism operably coupled with the tubular body.

18. The medical device of claim 1 wherein the medical device defines a catheter.

19. The medical device of claim 18 wherein the medical device further defines an ablation medical device.

20. The medical device of claim 18 wherein the medical device defines a diagnostic medical device.

21. The medical device of claim 1 wherein the medical device defines an internal cardiac defibrillator lead.

22. The medical device of claim 1 wherein the medical device defines a pacing lead.

23. The medical device of claim 1 further comprising one or more circuit elements coupled to an inner surface of the at least one printed circuit.

24. A flexible printed circuit board adapted for use with a medical device comprising:
   a flexible substrate defining a first section and a second section, the first section being narrower than the second section;
   the flexible substrate further defining at least one first conductive trace and at least one second conductive trace, the at least one first conductive trace being arranged generally angularly to the at least one second trace;
   the at least one first conductive trace is arranged along the first section of the flexible substrate; and
   the at least one second conductive trace is arranged generally longitudinally along at least a portion of the second section.

25. The flexible printed circuit of claim 24, the at least one first conductive trace being arranged generally perpendicular to the at least one second trace.

26. The flexible printed circuit of claim 25 wherein the at least one first conductive trace is electrically connected with the at least one second conductive trace.

27. The flexible printed circuit of claim 26 wherein the at least one first conductive trace comprises a plurality of conductive traces and wherein the at least one second conductive trace comprises a plurality of conductive traces and wherein each of the plurality of first conductive traces are only electrically connected with one of the plurality of second conductive traces.

28. The flexible printed circuit of claim 27 wherein the at least one first conductive trace is at least partially exposed.

29. The flexible printed circuit of claim 28 wherein the at least one second conductive trace is electrically isolated within the flexible printed circuit except for the connection to the at least one first conductive trace.

* * * * *